United States Patent
Newland et al.

(10) Patent No.: US 11,173,272 B2
(45) Date of Patent: Nov. 16, 2021

(54) GAS HUMIDIFICATION ARRANGEMENT

(71) Applicant: FISHER & PAYKEL HEALTHCARE LIMITED, Auckland (NZ)

(72) Inventors: Anthony James Newland, Auckland (NZ); Timothy James Beresford Sharp, Auckland (NZ); Jess Edward Donnelly, Auckland (NZ); Andre Van Schalkwyk, Auckland (NZ)

(73) Assignee: Fisher & Paykel Healthcare Limited, Auckland (NZ)

( * ) Notice: Subject to any disclaimer, the term of this patent is extended or adjusted under 35 U.S.C. 154(b) by 1391 days.

(21) Appl. No.: 15/303,719

(22) PCT Filed: May 1, 2015

(86) PCT No.: PCT/NZ2015/050049
§ 371 (c)(1),
(2) Date: Oct. 12, 2016

(87) PCT Pub. No.: WO2015/167347
PCT Pub. Date: Nov. 5, 2015

(65) Prior Publication Data
US 2017/0035985 A1   Feb. 9, 2017

Related U.S. Application Data

(60) Provisional application No. 61/987,979, filed on May 2, 2014.

(51) Int. Cl.
*A61M 16/16* (2006.01)
*A61M 16/00* (2006.01)
(Continued)

(52) U.S. Cl.
CPC ...... *A61M 16/161* (2014.02); *A61M 16/0066* (2013.01); *A61M 16/024* (2017.08);
(Continued)

(58) Field of Classification Search
CPC .......... A61M 16/16–168; A61M 16/18; A61M 16/109; F24F 6/06; F24F 6/105
See application file for complete search history.

(56) References Cited

U.S. PATENT DOCUMENTS 930,841 A * 8/1909 Collins ................. A61M 16/16
128/204.14
1,154,259 A  9/1915 Light
(Continued)

FOREIGN PATENT DOCUMENTS

AU  2002/244571  10/2002
AU  2007/317198  8/2013
(Continued)

OTHER PUBLICATIONS

International Search Report; PCT/NZ2015/050049; dated Jul. 29, 2015; 3 pages.

*Primary Examiner* — Samchuan C Yao
*Assistant Examiner* — Cana A Gallegos
(74) *Attorney, Agent, or Firm* — Knobbe, Martens, Olson, & Bear, LLP

(57) ABSTRACT

A humidification arrangement can be configured to have multiple compartments with each compartment having at least one moisture source and at least one heater. The compartments can be thermally isolated and can be controlled such that the moisture output of both the first and second compartments is set to a function of the same set of input signals.

33 Claims, 11 Drawing Sheets

(51) Int. Cl.
  *A61M 16/10* (2006.01)
  *A61M 16/20* (2006.01)
  *A61M 11/00* (2006.01)
  *A61M 11/04* (2006.01)

(52) U.S. Cl.
  CPC ...... *A61M 16/109* (2014.02); *A61M 16/1095* (2014.02); *A61M 16/16* (2013.01); *A61M 16/202* (2014.02); *A61M 11/001* (2014.02); *A61M 11/041* (2013.01); *A61M 2016/003* (2013.01); *A61M 2016/0027* (2013.01); *A61M 2016/103* (2013.01); *A61M 2016/1025* (2013.01); *A61M 2205/0283* (2013.01); *A61M 2205/0294* (2013.01); *A61M 2205/3368* (2013.01); *A61M 2205/3553* (2013.01); *A61M 2205/3569* (2013.01); *A61M 2205/3592* (2013.01); *A61M 2205/364* (2013.01); *A61M 2205/366* (2013.01); *A61M 2205/3633* (2013.01); *A61M 2205/3653* (2013.01); *A61M 2205/505* (2013.01); *A61M 2230/04* (2013.01); *A61M 2230/10* (2013.01); *A61M 2230/201* (2013.01); *A61M 2230/202* (2013.01); *A61M 2230/205* (2013.01)

(56) References Cited

U.S. PATENT DOCUMENTS

| | | | |
|---|---|---|---|
| 2,634,311 | A | 4/1953 | Darling |
| 2,745,074 | A | 5/1956 | Darling |
| 3,163,707 | A | 12/1964 | Darling |
| 3,283,580 | A | 11/1966 | Jacob et al. |
| 3,394,954 | A | 7/1968 | Sarns |
| 3,485,237 | A | 12/1969 | Bedford |
| 3,582,094 | A | 6/1971 | Whittaker |
| 3,588,859 | A | 6/1971 | Petree |
| 3,638,926 | A | 2/1972 | Melville et al. |
| 3,659,604 | A | 5/1972 | Melville et al. |
| 3,703,892 | A | 11/1972 | Meyers |
| 3,777,298 | A | 12/1973 | Newman |
| 3,903,742 | A | 9/1975 | Colton |
| 3,954,920 | A | 5/1976 | Heath |
| 3,987,133 | A | 10/1976 | Andra |
| 3,990,727 | A | 11/1976 | Gallagher |
| 4,028,444 | A | 6/1977 | Brown et al. |
| 4,038,519 | A | 7/1977 | Foucras |
| 4,060,576 | A | 11/1977 | Grant |
| 4,111,197 | A | 9/1978 | Warncke et al. |
| 4,139,762 | A | 2/1979 | Pohrer et al. |
| 4,172,709 | A | 10/1979 | Kippel et al. |
| 4,183,248 | A | 1/1980 | West |
| 4,333,451 | A | 6/1982 | Paluch |
| 4,473,923 | A | 10/1984 | Neroni et al. |
| 4,529,867 | A | 7/1985 | Velnosky et al. |
| 4,545,290 | A | 10/1985 | Lieberman |
| 4,564,748 | A | 1/1986 | Gupton |
| 4,588,425 | A | 5/1986 | Usry et al. |
| 4,621,632 | A | 11/1986 | Bartels et al. |
| 4,676,237 | A | 6/1987 | Wood et al. |
| 4,686,354 | A | 8/1987 | Makin |
| 4,708,831 | A | 11/1987 | Elsworth et al. |
| 4,774,032 | A | 9/1988 | Coates et al. |
| 4,813,280 | A | 3/1989 | Miller, Jr. et al. |
| 4,844,512 | A | 7/1989 | Gahwiler |
| 4,942,877 | A | 7/1990 | Sakai et al. |
| 4,944,310 | A | 7/1990 | Sullivan |
| 4,967,744 | A | 11/1990 | Chua |
| 5,031,612 | A | 7/1991 | Clementi |
| 5,058,588 | A | 10/1991 | Kaestle |
| 5,060,506 | A | 10/1991 | Douglas |
| 5,117,819 | A | 6/1992 | Servidio et al. |
| 5,134,996 | A | 8/1992 | Bell |
| 5,148,801 | A | 9/1992 | Douwens et al. |
| 5,213,376 | A | 5/1993 | Szabo |
| RE34,599 | E | 5/1994 | Suszynski et al. |
| 5,357,948 | A | 10/1994 | Szabo |
| 5,367,604 | A | 11/1994 | Murray |
| 5,392,770 | A | 2/1995 | Clawson et al. |
| 5,454,061 | A | 9/1995 | Carlson |
| 5,483,616 | A | 1/1996 | Chiu et al. |
| 5,537,996 | A | 7/1996 | McPhee |
| 5,551,883 | A | 9/1996 | Davis |
| 5,640,951 | A | 6/1997 | Huddart et al. |
| 5,660,567 | A | 8/1997 | Nierlich et al. |
| 5,720,293 | A | 2/1998 | Quinn et al. |
| 5,778,872 | A | 7/1998 | Fukunaga et al. |
| 5,906,201 | A | 5/1999 | Nilson |
| 5,943,473 | A | 8/1999 | Levine |
| D419,522 | S | 1/2000 | Kamagai |
| 6,039,696 | A | 3/2000 | Bell |
| 6,053,482 | A | 4/2000 | Glenn et al. |
| 6,078,729 | A | 6/2000 | Pel |
| 6,102,037 | A | 8/2000 | Koch |
| 6,105,970 | A | 8/2000 | Siegrist et al. |
| 6,126,610 | A | 10/2000 | Rich et al. |
| 6,138,674 | A | 10/2000 | Gull et al. |
| 6,196,980 | B1 | 3/2001 | Akerfeldt et al. |
| 6,201,983 | B1 | 3/2001 | Haumann et al. |
| 6,226,451 | B1 | 5/2001 | Wong |
| 6,349,722 | B1 | 2/2002 | Gradon et al. |
| 6,360,741 | B2 | 3/2002 | Truschel |
| 6,402,207 | B1 | 6/2002 | Segal et al. |
| 6,435,180 | B1 | 8/2002 | Hewson et al. |
| 6,467,477 | B1 | 10/2002 | Frank et al. |
| 6,508,249 | B2 | 1/2003 | Hoenig |
| 6,511,075 | B1 | 1/2003 | Schmidt |
| 6,551,143 | B2 | 4/2003 | Tanaka et al. |
| 6,554,260 | B1 | 4/2003 | Lipscombe et al. |
| 6,591,061 | B2 | 7/2003 | Wang |
| 6,598,604 | B1 | 7/2003 | Seakins |
| 6,612,624 | B1 | 9/2003 | Segal et al. |
| 6,648,669 | B1 | 11/2003 | Kim et al. |
| 6,668,828 | B1 | 12/2003 | Figley et al. |
| 6,685,491 | B2 | 2/2004 | Gergek |
| 6,827,084 | B2 | 12/2004 | Grubb, Jr. |
| 6,827,340 | B2 | 12/2004 | Austin et al. |
| 6,874,771 | B2 | 4/2005 | Birdsell et al. |
| 6,895,803 | B2 | 5/2005 | Seakins et al. |
| 6,918,389 | B2 | 7/2005 | Seakins et al. |
| 6,935,337 | B2 | 8/2005 | Virr et al. |
| 6,943,566 | B2 | 9/2005 | Florin et al. |
| 6,953,354 | B2 | 10/2005 | Edirisuriya et al. |
| 7,043,979 | B2 | 5/2006 | Smith et al. |
| 7,063,668 | B2 | 6/2006 | Cardelius et al. |
| 7,086,422 | B2 | 8/2006 | Huber et al. |
| 7,090,541 | B1 | 8/2006 | Ho |
| 7,096,864 | B1 | 8/2006 | Mayer et al. |
| 7,120,354 | B2 | 10/2006 | Mackie et al. |
| 7,137,654 | B2 | 11/2006 | Segal et al. |
| 7,140,367 | B2 | 11/2006 | White et al. |
| 7,157,035 | B2 | 1/2007 | Edirisuriya et al. |
| 7,191,780 | B2 | 3/2007 | Faram |
| 7,225,809 | B1 | 6/2007 | Bowen et al. |
| 7,284,554 | B2 | 10/2007 | Shaw |
| 7,327,547 | B1 | 2/2008 | Epstein |
| 7,327,949 | B1 | 2/2008 | Cheng et al. |
| 7,334,587 | B2 | 2/2008 | Lake |
| 7,364,436 | B2 | 4/2008 | Yen |
| 7,396,995 | B2 | 7/2008 | Laurent et al. |
| 7,448,383 | B2 | 11/2008 | Delache et al. |
| 7,478,635 | B2 | 1/2009 | Wixey et al. |
| 7,525,663 | B2 | 4/2009 | Kwok et al. |
| 7,637,288 | B2 | 12/2009 | Kressierer/Huber et al. |
| 7,677,246 | B2 | 3/2010 | Kepler et al. |
| 7,766,050 | B2 | 8/2010 | Patel |
| 7,794,426 | B2 | 9/2010 | Briones et al. |
| 7,814,907 | B2 | 10/2010 | Brenner et al. |
| D628,288 | S | 11/2010 | Row et al. |
| 7,827,981 | B2 | 11/2010 | Bamford |
| 7,870,857 | B2 | 1/2011 | Dhuper et al. |
| 7,913,689 | B2 | 3/2011 | Henry et al. |
| 7,942,380 | B2 | 5/2011 | Bertinetti et al. |
| 7,942,389 | B2 | 5/2011 | Koch et al. |

(56) References Cited

U.S. PATENT DOCUMENTS

| | | |
|---|---|---|
| 7,965,930 B2 | 6/2011 | Carlson et al. |
| 7,983,542 B2 | 7/2011 | McGhin et al. |
| 7,987,847 B2 | 8/2011 | Wickham |
| 7,992,554 B2 | 8/2011 | Radomski et al. |
| 7,997,267 B2 | 8/2011 | Ging et al. |
| 8,025,849 B2 | 9/2011 | Baldwin et al. |
| 8,059,947 B2 | 11/2011 | Bradley et al. |
| 8,063,343 B2 | 11/2011 | McGhin et al. |
| 8,078,040 B2 | 12/2011 | Forrester |
| 8,100,124 B2 | 1/2012 | Becker et al. |
| 8,122,882 B2 | 2/2012 | McGhin et al. |
| 8,136,521 B2 | 3/2012 | Matthews et al. |
| 8,137,082 B2 | 3/2012 | Campbell |
| 8,181,940 B2 | 5/2012 | Payne et al. |
| 8,182,144 B2 | 5/2012 | Koch |
| 8,186,345 B2 | 5/2012 | Payton et al. |
| 8,186,352 B2 | 5/2012 | Gunaratnam et al. |
| 8,197,123 B2 | 6/2012 | Snyder et al. |
| 8,221,530 B2 | 7/2012 | Peter et al. |
| 8,245,709 B2 | 8/2012 | Rossen et al. |
| 8,245,710 B2 | 8/2012 | Makinson et al. |
| 8,253,076 B2 | 8/2012 | Andel et al. |
| 8,257,286 B2 | 9/2012 | Meyer et al. |
| 8,267,084 B2 | 9/2012 | Kwok |
| 8,287,517 B2 | 10/2012 | Hanlon et al. |
| 8,316,848 B2 | 11/2012 | Kwok et al. |
| 8,333,194 B2 | 12/2012 | Lewis et al. |
| 8,333,199 B2 | 12/2012 | Landis et al. |
| 8,355,753 B2 | 1/2013 | Bochenko et al. |
| 8,360,059 B2 | 1/2013 | Koulechov et al. |
| 8,365,726 B2 | 2/2013 | Snow et al. |
| 8,381,724 B2 | 2/2013 | Bowen et al. |
| 8,424,514 B2 | 4/2013 | Oates et al. |
| 8,453,641 B2 | 6/2013 | Payton et al. |
| 8,453,643 B2 | 6/2013 | Sanchez et al. |
| 8,469,025 B2 | 6/2013 | Mayer et al. |
| 8,490,621 B2 | 7/2013 | Radomski et al. |
| 8,496,001 B2 | 7/2013 | Schermeier et al. |
| RE44,453 E | 8/2013 | Virr et al. |
| 8,511,305 B2 | 8/2013 | Liu et al. |
| 8,511,651 B2 | 8/2013 | Fridberg et al. |
| 8,522,782 B2 | 9/2013 | Lewis et al. |
| 8,528,552 B2 | 9/2013 | Blumenthal |
| 8,544,465 B2 | 10/2013 | Smith et al. |
| 8,550,072 B2 | 10/2013 | Thudor et al. |
| 8,631,789 B2 | 1/2014 | Virr et al. |
| 8,640,696 B2 | 2/2014 | Pujol et al. |
| 8,733,348 B2 | 5/2014 | Korneff et al. |
| 8,733,349 B2 | 5/2014 | Bath et al. |
| 8,770,190 B2 | 7/2014 | Doherty et al. |
| 8,800,970 B2 | 8/2014 | Heine et al. |
| 8,844,521 B2 | 9/2014 | McCarthy |
| 8,851,071 B2 | 10/2014 | Kuo et al. |
| 8,905,023 B2 | 12/2014 | Niland et al. |
| 8,915,250 B2 | 12/2014 | Dugan et al. |
| 8,931,481 B2 | 1/2015 | Jones et al. |
| 8,939,147 B2 | 1/2015 | Henryetai. |
| 8,985,105 B2 | 3/2015 | Burton et al. |
| 9,022,946 B2 | 5/2015 | Haque |
| 9,067,036 B2 | 6/2015 | Korneff et al. |
| 9,119,933 B2 | 9/2015 | Bedford et al. |
| 9,132,252 B2 | 9/2015 | Barlow et al. |
| 9,162,035 B2 | 10/2015 | Kwok |
| 9,186,477 B2 | 11/2015 | Hunt et al. |
| 9,205,220 B2 | 12/2015 | Korneff et al. |
| 9,212,673 B2 | 12/2015 | Korneff et al. |
| 9,242,064 B2 | 1/2016 | Rustad et al. |
| 9,254,368 B2 | 2/2016 | Blumenthal et al. |
| 9,289,572 B2 | 3/2016 | Korneff et al. |
| RE46,079 E | 7/2016 | Virr et al. |
| 9,381,317 B2 | 7/2016 | Landis et al. |
| 9,387,299 B2 | 7/2016 | Zwolinsky et al. |
| 9,427,547 B2 | 8/2016 | Landis et al. |
| 9,446,210 B2 | 9/2016 | Orr et al. |
| 9,517,321 B2 | 12/2016 | Buechi et al. |
| 9,545,493 B2 | 1/2017 | Mayer et al. |
| 9,566,409 B2 | 2/2017 | Gründler et al. |
| 9,572,949 B2 | 2/2017 | Vos et al. |
| 9,572,951 B2 | 2/2017 | Barker et al. |
| 9,586,019 B2 | 3/2017 | Heine et al. |
| 9,642,979 B2 | 5/2017 | Korneff et al. |
| 9,838,759 B2 | 12/2017 | Kirmse et al. |
| 9,861,778 B2 | 1/2018 | Bath et al. |
| 9,937,314 B2 | 4/2018 | Buechi et al. |
| 9,937,316 B2 | 4/2018 | Buechi et al. |
| 10,046,136 B2 | 8/2018 | Pujol |
| 2001/0017134 A1 | 8/2001 | Bahr |
| 2001/0050080 A1 | 12/2001 | Seakins et al. |
| 2002/0100320 A1 | 8/2002 | Smith et al. |
| 2003/0148664 A1 | 8/2003 | Cheng |
| 2003/0200727 A1 | 10/2003 | Kim |
| 2003/0236015 A1 | 12/2003 | Edirisuriya et al. |
| 2004/0074493 A1 | 4/2004 | Seakins et al. |
| 2004/0087213 A1 | 5/2004 | Kao |
| 2004/0149284 A1 | 8/2004 | Smith et al. |
| 2004/0221843 A1 | 11/2004 | Baecke |
| 2004/0239001 A1 | 12/2004 | Edirisuriya et al. |
| 2004/0244858 A1 | 12/2004 | Jeong |
| 2006/0030191 A1 | 2/2006 | Tuin et al. |
| 2006/0081247 A1* | 4/2006 | Britt ............... A61M 16/16 128/203.16 |
| 2006/0118113 A1 | 6/2006 | Bremner et al. |
| 2006/0137445 A1 | 6/2006 | Smith et al. |
| 2006/0237012 A1 | 10/2006 | Thudor et al. |
| 2007/0039374 A1 | 2/2007 | Borali |
| 2007/0079982 A1 | 4/2007 | Laurent et al. |
| 2007/0107737 A1 | 5/2007 | Landis et al. |
| 2007/0144519 A1 | 6/2007 | Henry et al. |
| 2007/0175473 A1 | 8/2007 | Lewis et al. |
| 2007/0248934 A1 | 10/2007 | Mosimann |
| 2007/0272239 A1 | 11/2007 | Aylsworth et al. |
| 2007/0284361 A1 | 12/2007 | Nadjafizadeh et al. |
| 2008/0000474 A1 | 1/2008 | Jochle et al. |
| 2008/0051674 A1 | 2/2008 | Davenport et al. |
| 2008/0066751 A1 | 3/2008 | Polacsek |
| 2008/0105257 A1 | 5/2008 | Klasek et al. |
| 2008/0142019 A1 | 6/2008 | Lewis et al. |
| 2008/0202512 A1 | 8/2008 | Kressierer-Huber |
| 2008/0251073 A1 | 10/2008 | Jassell et al. |
| 2009/0050150 A1 | 2/2009 | Rossen et al. |
| 2009/0107493 A1 | 4/2009 | Liu et al. |
| 2009/0107496 A1 | 4/2009 | McGhin et al. |
| 2009/0107501 A1 | 4/2009 | Krieger |
| 2009/0107981 A1 | 4/2009 | Andel et al. |
| 2009/0110022 A1 | 4/2009 | Snyder et al. |
| 2009/0110378 A1 | 4/2009 | Bradley et al. |
| 2009/0174092 A1 | 7/2009 | Kwok et al. |
| 2009/0223514 A1 | 9/2009 | Smith et al. |
| 2009/0301482 A1 | 12/2009 | Burton et al. |
| 2009/0320840 A1 | 12/2009 | Klasek et al. |
| 2010/0102799 A1 | 4/2010 | Schnidrig |
| 2010/0116272 A1 | 5/2010 | Row et al. |
| 2010/0147301 A1 | 6/2010 | Kwok |
| 2010/0154796 A1 | 6/2010 | Smith et al. |
| 2010/0242963 A1 | 9/2010 | Brieger et al. |
| 2011/0023874 A1 | 2/2011 | Bath et al. |
| 2011/0046433 A1 | 2/2011 | Khodak |
| 2011/0046494 A1 | 2/2011 | Balji et al. |
| 2011/0088693 A1 | 4/2011 | Somervell et al. |
| 2011/0108031 A1 | 5/2011 | Korneff et al. |
| 2011/0114093 A1 | 5/2011 | Patil et al. |
| 2011/0155132 A1 | 6/2011 | Virr et al. |
| 2011/0247623 A1 | 10/2011 | McCarthy |
| 2011/0253136 A1 | 10/2011 | Sweeney et al. |
| 2011/0273505 A1* | 11/2011 | Horiba ............... B41J 2/16552 347/17 |
| 2011/0283999 A2 | 11/2011 | Smith et al. |
| 2011/0308518 A1 | 12/2011 | McGroary et al. |
| 2011/0313689 A1 | 12/2011 | Holley et al. |
| 2011/0316562 A1 | 12/2011 | Cefai et al. |
| 2012/0060838 A1 | 3/2012 | Lapoint et al. |
| 2012/0125333 A1 | 5/2012 | Bedford et al. |
| 2012/0146251 A1 | 6/2012 | Heine et al. |
| 2012/0174924 A1 | 7/2012 | Smith et al. |

(56) References Cited

U.S. PATENT DOCUMENTS

| | | |
|---|---|---|
| 2012/0215125 A1 | 8/2012 | Orr et al. |
| 2012/0227738 A1 | 9/2012 | Virr et al. |
| 2012/0255758 A1 | 10/2012 | Lee |
| 2012/0285448 A1 | 11/2012 | Dugan et al. |
| 2013/0008158 A1 | 1/2013 | Hon |
| 2013/0042867 A1 | 2/2013 | Kwok et al. |
| 2013/0043677 A1 | 2/2013 | Gibson |
| 2013/0087143 A1 | 4/2013 | Pujol |
| 2013/0104888 A1 | 5/2013 | Landis et al. |
| 2013/0104901 A1 | 5/2013 | Landis et al. |
| 2013/0112202 A1 | 5/2013 | Fogelbrink |
| 2013/0174839 A1 | 7/2013 | Ging et al. |
| 2013/0206140 A1 | 8/2013 | Kepler et al. |
| 2013/0239966 A1 | 9/2013 | Klasek et al. |
| 2013/0247905 A1 | 9/2013 | Miller et al. |
| 2013/0255677 A1 | 10/2013 | Varga |
| 2013/0269693 A1 | 10/2013 | Neatrour et al. |
| 2013/0333701 A1 | 12/2013 | Herron |
| 2013/0340752 A1 | 12/2013 | Landis et al. |
| 2014/0020684 A1 | 1/2014 | Klasek et al. |
| 2014/0116433 A1 | 5/2014 | Ghalib et al. |
| 2014/0130802 A1 | 5/2014 | Virr et al. |
| 2014/0202460 A1 | 7/2014 | Bath et al. |
| 2014/0216446 A1 | 8/2014 | Wruck |
| 2014/0251322 A1 | 9/2014 | Miller |
| 2014/0251331 A1 | 9/2014 | Korneff et al. |
| 2014/0305431 A1* | 10/2014 | Holley .............. A61M 16/0003 128/201.13 |
| 2014/0311489 A1 | 10/2014 | Heine et al. |
| 2014/0318536 A1 | 10/2014 | Landis et al. |
| 2014/0338666 A1 | 11/2014 | Visveshwara et al. |
| 2014/0345614 A1 | 11/2014 | Kwok |
| 2014/0366876 A1 | 12/2014 | Huby et al. |
| 2014/0368574 A1* | 12/2014 | La Vos ................ B41J 2/16552 347/25 |
| 2014/0374243 A1* | 12/2014 | Lin .......................... C25B 9/00 204/228.3 |
| 2015/0031939 A1* | 1/2015 | Avery ................ A61M 16/161 600/22 |
| 2015/0040897 A1 | 2/2015 | Buechi |
| 2015/0048530 A1 | 2/2015 | Cheung et al. |
| 2015/0083126 A1 | 3/2015 | Rogers |
| 2015/0083132 A1 | 3/2015 | Jones et al. |
| 2015/0090260 A1 | 4/2015 | Seakins et al. |
| 2015/0107588 A1 | 4/2015 | Cheung et al. |
| 2015/0144130 A1 | 5/2015 | O'Donnell et al. |
| 2015/0196725 A1 | 7/2015 | Oates et al. |
| 2015/0359990 A1 | 12/2015 | Barker et al. |
| 2016/0008560 A1 | 1/2016 | Kwok |
| 2016/0015927 A1 | 1/2016 | Winski et al. |
| 2016/0022954 A1 | 1/2016 | Bath et al. |
| 2016/0051789 A1 | 2/2016 | Korneff et al. |
| 2016/0089510 A1 | 3/2016 | Korneff et al. |
| 2016/0101258 A1 | 4/2016 | Rustad et al. |
| 2016/0199612 A1 | 7/2016 | Foote et al. |
| 2016/0256642 A1 | 9/2016 | Soysa et al. |
| 2016/0256657 A1 | 9/2016 | Klasek et al. |
| 2016/0296721 A1 | 10/2016 | Landis et al. |
| 2016/0310691 A1 | 10/2016 | Bath et al. |
| 2016/0367776 A1 | 12/2016 | Landis et al. |
| 2016/0367779 A1 | 12/2016 | Landis et al. |
| 2017/0095635 A1 | 4/2017 | Huby |
| 2017/0136198 A1 | 5/2017 | Delangre et al. |
| 2017/0161461 A1 | 6/2017 | Delangre et al. |
| 2017/0173293 A1 | 6/2017 | Osborne et al. |
| 2017/0239432 A1 | 8/2017 | Delangre et al. |
| 2017/0326320 A1 | 11/2017 | Baigent et al. |
| 2018/0078730 A1 | 3/2018 | Bath et al. |
| 2018/0169361 A1 | 6/2018 | Dennis et al. |
| 2018/0250491 A1 | 9/2018 | Row et al. |

FOREIGN PATENT DOCUMENTS

| | | |
|---|---|---|
| AU | 2010/206053 | 8/2014 |
| CA | 2495451 | 8/2011 |
| CN | 1598510 | 3/2005 |
| DE | 3110903 | 9/1982 |
| DE | 3618614 | 12/1987 |
| DE | 4020522 | 1/1992 |
| DE | 4102223 | 7/1992 |
| DE | 19647548 | 5/1998 |
| DE | 19958296 | 9/2001 |
| DE | 20 2004 006 484.7 | 9/2005 |
| DE | 10 2004 030 747 | 1/2006 |
| DE | 20 2005 008 152.3 | 10/2006 |
| DE | 20 2005 008 156.6 | 10/2006 |
| DE | 203 21 468.4 | 8/2007 |
| DE | 203 21 469.2 | 8/2007 |
| DE | 203 21 470.6 | 8/2007 |
| DE | 203 21 471.4 | 8/2007 |
| DE | 203 21 472.2 | 8/2007 |
| DE | 20 2006 007 397.3 | 9/2007 |
| DE | 20 2006 011 754.7 | 12/2007 |
| DE | 201 22 844.0 | 5/2008 |
| DE | 10 2007 003 454 | 7/2008 |
| DE | 10 2007 003 455 | 8/2008 |
| DE | 10 2007 039 391 | 2/2009 |
| DE | 10 2008 001 022 | 10/2009 |
| DE | 20 2004 021 757.0 | 9/2010 |
| DE | 20 2004 021 758.9 | 9/2010 |
| DE | 201 22 937.4 | 9/2010 |
| DE | 20 2004 021 756.2 | 10/2010 |
| DE | 20 2004 021 759.7 | 10/2010 |
| DE | 20 2004 021 774.0 | 11/2010 |
| DE | 20 2004 021 777.5 | 12/2010 |
| DE | 20 2004 021 794.5 | 2/2011 |
| DE | 20 2004 021 795.3 | 2/2011 |
| DE | 20 2004 021 796.1 | 2/2011 |
| DE | 20 2004 021 798.8 | 2/2011 |
| DE | 20 2006 020 951.4 | 2/2011 |
| DE | 20 2006 020 952.4 | 2/2011 |
| DE | 20 2004 021 829.1 | 5/2011 |
| DE | 201 22 943.9 | 5/2011 |
| DE | 201 22 944.7 | 5/2011 |
| DE | 201 22 945.5 | 5/2011 |
| DE | 20 2005 021 927.4 | 6/2011 |
| DE | 20 2006 021 019.9 | 11/2011 |
| DE | 203 21 882.5 | 12/2011 |
| DE | 20 2004 021 876.3 | 1/2012 |
| DE | 20 2007 019 350.5 | 1/2012 |
| DE | 20 2011 107 902.7 | 1/2012 |
| DE | 20 2010 016 037.5 | 3/2012 |
| DE | 20 2012 007 229.3 | 10/2012 |
| EP | 0201985 | 11/1986 |
| EP | 0291921 | 10/1991 |
| EP | 0535952 | 4/1993 |
| EP | 0567158 | 10/1993 |
| EP | 0885623 | 12/1998 |
| EP | 1262208 | 12/2002 |
| EP | 1352670 | 10/2003 |
| EP | 1646910 | 4/2006 |
| EP | 1669098 | 6/2006 |
| EP | 1683066 | 7/2006 |
| EP | 1741462 | 1/2007 |
| EP | 1924311 | 5/2008 |
| EP | 2079505 | 7/2009 |
| EP | 2089086 | 8/2009 |
| EP | 2195061 | 6/2010 |
| EP | 2229973 | 9/2010 |
| EP | 2236167 | 10/2010 |
| EP | 2282795 | 2/2011 |
| EP | 2307082 | 4/2011 |
| EP | 2335761 | 6/2011 |
| EP | 2340867 | 7/2011 |
| EP | 2355881 | 8/2011 |
| EP | 2371409 | 10/2011 |
| EP | 2415445 | 2/2012 |
| EP | 2471568 | 7/2012 |
| EP | 2498854 | 9/2012 |
| EP | 2514478 | 10/2012 |

(56) References Cited

FOREIGN PATENT DOCUMENTS

| | | |
|---|---|---|
| EP | 2575944 | 4/2013 |
| EP | 2640451 | 9/2013 |
| EP | 2651481 | 10/2013 |
| EP | 2654869 | 10/2013 |
| EP | 2667919 | 12/2013 |
| EP | 2760516 | 8/2014 |
| EP | 2830695 | 2/2015 |
| EP | 2877224 | 6/2015 |
| EP | 3053623 | 8/2016 |
| GB | 1310949 | 3/1973 |
| GB | 1364127 | 8/1974 |
| GB | 2176313 | 12/1986 |
| JP | H03194747 | 8/1991 |
| JP | H0623051 | 3/1994 |
| JP | H11248076 | 9/1999 |
| JP | 2001-095920 | 4/2001 |
| JP | 2003-275312 | 9/2003 |
| JP | 4242816 | 3/2009 |
| NZ | 564886 | 2/2011 |
| NZ | 586325 | 1/2012 |
| NZ | 597020 | 6/2013 |
| NZ | 604137 | 6/2014 |
| NZ | 625605 | 4/2016 |
| NZ | 710078 | 1/2017 |
| NZ | 710351 | 1/2017 |
| NZ | 631008 | 7/2017 |
| NZ | 733931 | 2/2019 |
| WO | WO 97/018001 | 5/1997 |
| WO | WO 2000/029057 | 5/2000 |
| WO | WO 2001/032069 | 5/2001 |
| WO | WO 01/97894 | 12/2001 |
| WO | WO 02/066106 | 8/2002 |
| WO | WO 02/66107 | 8/2002 |
| WO | WO 2004/011072 | 2/2004 |
| WO | WO 2005/011785 | 2/2005 |
| WO | WO 2005/021076 | 3/2005 |
| WO | WO 2007/051230 | 5/2007 |
| WO | WO 2008/055308 | 5/2008 |
| WO | WO 2008/058328 | 5/2008 |
| WO | WO 2008/060295 | 5/2008 |
| WO | WO 2008/076230 | 6/2008 |
| WO | WO 2009/022004 | 2/2009 |
| WO | WO 2010/031125 | 3/2010 |
| WO | WO 2010/031126 | 3/2010 |
| WO | WO 2012/065999 | 10/2012 |
| WO | WO 2012/164407 | 12/2012 |
| WO | WO 2013/050907 | 4/2013 |
| WO | WO 2013/026901 | 5/2013 |
| WO | WO 2013/045575 | 5/2013 |
| WO | WO 2013/049660 | 5/2013 |
| WO | WO 2013/127474 | 9/2013 |
| WO | WO 2014/055407 | 4/2014 |
| WO | WO 2014/077706 | 5/2014 |
| WO | WO 2014/205513 | 12/2014 |
| WO | WO 2015/060729 | 4/2015 |
| WO | WO 2015/160268 | 10/2015 |
| WO | WO 2016/042522 | 3/2016 |
| WO | WO 2016/089224 | 6/2016 |
| WO | WO 2016/139645 | 9/2016 |
| WO | WO 2017/027906 | 2/2017 |
| WO | WO 2017/126980 | 7/2017 |

* cited by examiner

GAS HUMIDIFICATION ARRANGEMENT

INCORPORATION BY REFERENCE

Any and all applications for which a foreign or domestic priority claim is identified in the Application Data Sheet as filed with the present application are hereby incorporated by reference under 37 CFR 1.57.

The present application claims priority benefit of U.S. Provisional Application No. 61/987,979, filed on May 2, 2014, which is hereby incorporated by reference in its entirety.

BACKGROUND

1. Technical Field

The present disclosure generally relates to gas therapy systems. More particularly, the present disclosure relates to humidification arrangements for use with gas therapy systems.

2. Description of the Related Art

A patient dealing with respiratory illness, for example, chronic obstructive pulmonary disease (COPD), can have difficulty engaging in effective respiration. This difficulty may be the result of a variety of physiological faults, including a breakdown of lung tissue, dysfunctions of the small airways, excessive accumulation of sputum, infection, genetic disorders, or cardiac insufficiency.

With such illnesses, it is useful to provide the patient with a therapy that can improve the ventilation of the patient. In some situations, the patient can be provided with a respiratory therapy system that includes a gas source, an interface that may be used to transmit gas to an airway of a patient, and a conduit extending between the gas source and the interface.

Gas delivered to an airway of the patient from the gas source can help to promote adequate ventilation of the patient. The gas source may be, for example, a container of air and/or another gas suitable for inspiration, for example, oxygen or nitric oxide, a mechanical blower capable of propelling a gas through the conduit to the interface, or some combination of these.

The respiratory therapy system can include a gas humidification system that can humidify and heat gases passing through the respiratory therapy system to improve patient comfort and/or improve the prognosis of the patient's respiratory illness. The gas humidification system can include a water reservoir and a heating element for heating the water in the reservoir. As the water heats up, water vapor is formed that can join the stream of gases passing through the gas humidification system. Gas humidification systems can also be utilized for other applications where the humidification of gases may be useful, including the humidification of insufflation gases used in laparoscopic surgery.

Although gas humidification systems are useful, obtaining fine control of the moisture contribution of a gas humidification system to a given gas flow can be difficult. If the respiratory therapy system is configured to deliver a gas at a high gas flow rate, a gas humidification system with a relatively large exposed surface area of water (which may necessitate a relatively large volume of water if the water is not replenished during a session of use) and a powerful heating element may be required to provide an adequate level of moisture to the gas. However, if the gas flow rate of the delivered gas changes (for example, drops to a lower level), the hysteresis of the moisture output of the gas humidification system (which could be at least in part due to the large thermal mass of the relatively large volume of water) may cause changes in moisture output to proceed more slowly than desired. Additionally, at lower gas flow rates, the powerful heating element may cause some undesired variation in the output of the gas humidification system (for example, reduced output stability with respect to a desired output condition), particularly if the volume of water in the gas humidification system is relatively low. However, if a relatively small volume of water and a relatively less powerful heating element is used, although good control of moisture output may be achieved at lower gas flows, inadequate levels of moisture output may be achieved at higher gas flows.

SUMMARY

Certain features, aspects, and advantages of at least one of the configurations disclosed herein include the realization that a gas humidification system may comprise multiple stages with each stage comprising a water reservoir and a heating element for heating water in the water reservoir. The heating elements may be controlled according to a single set of input conditions such that the heating elements may work in synchronicity to provide adequate humidity to a flow of gas for a range of flow rates while providing at least some stability for the humidity output of the gas humidification system in light of rapidly changing input conditions. In some cases, the heating elements may be controlled such that the gas output temperature or humidity of a first stage of the gas humidification system can affect the operation of a heating element of another stage of the gas humidification system downstream of the first stage.

Thus, in accordance with certain features, aspects and advantages of at least one of the embodiments disclosed herein, a humidification arrangement is disclosed. The humidification arrangement may comprise a gas passageway extending between a first location and a second location, the gas passageway comprising a first compartment and a second compartment, each compartment comprising a moisture source configured to add moisture to gases in the gas passageway, each moisture source having an adjustable moisture output, wherein (a) both the moisture output of the first compartment and the moisture output of the second compartment are set to a function of an input signal received by a controller controlling the humidification arrangement, or (b) the moisture output of the second compartment is set to a function of an input or output signal received or sent by a controller controlling the first compartment.

In some configurations, at least one of the compartments may comprise a heater having an adjustable heat output, the heater adapted to heat the moisture source, wherein the heat output of each heater is set to a function of an input signal received by a controller controlling the humidification arrangement.

In some configurations, the first compartment may comprise a first heater having an adjustable heat output with the heater being adapted to heat the moisture source of the first compartment, wherein the heat output of the first heater is set to a function of an input or output signal received or sent by a controller controlling the second compartment.

In some configurations, the second compartment may be downstream of the first compartment.

In some configurations, the gas passageway of the humidification arrangement may be substantially isolated from the environment outside of the humidification arrangement.

In some configurations, the first compartment may be thermally isolated from the second compartment. A partition could be used to separate the first compartment from the second compartment.

In some configurations, the humidification arrangement may be contained within a single housing. In some configurations, the first and second compartments may be contained within a single housing. In some configurations, the humidification arrangement may be contained within multiple housings. In some configurations, the first and second compartments may be contained within separate housings.

In some configurations, the humidification arrangement may comprise one or more additional compartments. Each additional compartment may comprise a moisture source configured to add moisture to gases in the gas passageway, and each moisture source may have an adjustable moisture output.

In some configurations, the first and second compartments may be linked by a section of tubing. The section of tubing may comprise a tube heater. The tube heater may have an adjustable heat output, and the heat output of the tube heater may be a function of an input or output signal of a controller controlling the humidification arrangement, the first compartment, and/or the second compartment.

In some configurations, the humidification arrangement may comprise a conduit extending from the second location to a patient interface. The conduit may comprise a flow rate sensing module. The flow rate sensing module may be on an exterior surface of the conduit. The flow rate sensing module may comprise an omnidirectional flow sensor. The conduit may comprise a conduit heater. The conduit heater may have an adjustable heat output. The heat output of the conduit heater may be set to a function of an output signal of the flow rate sensing module. The conduit heater may also be set to a function of an input or output signal of a controller controlling the humidification arrangement, the first compartment, and/or the second compartment.

In some configurations, at least one of the moisture sources may comprise a liquid reservoir. In some configurations, at least one of the moisture sources may comprise a hydrophilic material at least partially imbued with a liquid.

In some configurations, at least one of the compartments may comprise a movable panel. The movable panel can be configured to at least partially occlude a surface of the moisture source that interfaces with gases passing through the gas passageway. In some such configurations, the movement of the panel may be electromechanically actuated. In some such configurations, the movement of the panel may be a function of an input or output signal received or sent by a controller controlling the humidification arrangement, the first compartment, and/or the second compartment.

Additionally, in accordance with certain features, aspects and advantages of at least one of the embodiments disclosed herein, a method of humidifying a gas is disclosed. Gas may be passed through a humidification arrangement comprising a gas passageway extending between a first location and a second location. The gas passageway may comprise a first compartment and a second compartment, each compartment comprising a moisture source configured to add moisture to gases in the gas passageway, the moisture source having an adjustable moisture output, wherein (a) both the moisture output of the first compartment and the moisture output of the second compartment are set to a function of an input signal received by a controller controlling the humidification arrangement, or (b) the moisture output of the second compartment is set to a function of an input or output signal received or sent by a controller controlling the first compartment. In some configurations, the gas humidification systems mentioned above may be used with this method.

In some configurations, a humidification arrangement comprises a gas passageway extending between a first location and a second location. The gas passageway comprises a first compartment and a second compartment. Each compartment comprises a moisture source configured to add moisture to gases in the gas passageway. Each moisture source has an adjustable moisture output. The humidification arrangement further comprises a sensor that is adapted to sense one or more characteristic or substance of a gases flow. A controller is adapted to use data from the sensor to control the adjustable moisture output of at least one of the first compartment and the second compartment to deliver a target gas characteristic or substance.

In some such configurations, the moisture source of the first compartment and the moisture source of the second compartment are separate from each other.

In some such configurations, the moisture source of the first compartment and the moisture source of the second compartment are in fluid communication with each other.

In some such configurations, a heater is configured to heat at least one of the first compartment and the second compartment. In some such configurations, the heater is configured to heat the first compartment and the second compartment.

In some such configurations, the first compartment and the second compartment are integrated into a single housing. In some such configurations, the first compartment and the second compartment are isolated from each other by a partition. In some such configurations, the first compartment and the second compartment are thermally isolated from each other.

In some such configurations, the first compartment is defined within a first housing and the second compartment is defined within a second housing, and the first housing is separate and distinct from the second housing.

In some such configurations, at least one of the first compartment and the second compartment is configured to provide a medicament to the gases flow.

In some such configurations, the first compartment and the second compartment are arranged in series along the gas passageway.

In some such configurations, the gas passageway comprises a tube that connects the first compartment to the second compartment. In some such configurations, the tube connects an outlet of the first compartment to an inlet of the second compartment.

In some such configurations, the gas passageway comprises a fixed arrangement.

In some such configurations, the gas passageway comprises one or more valves that direct flow through the humidification arrangement.

In some such configurations, the sensor is positioned adjacent to a port of the humidification arrangement. In some such configurations, the port is an outlet of the humidification arrangement.

In some such configurations, the sensor is positioned adjacent to the first chamber or the second chamber.

In some such configurations, the sensor is positioned to be in fluid communication with the gases passageway adjacent a passage into or out of the first compartment or the second compartment.

In some such configurations, the sensor is positioned to be in fluid communication with the gases passageway at a location between a first compartment passageway and a second compartment passageway. In some such configurations, the first compartment and the second compartment are connected in series.

In some such configurations, the sensor is adapted to measure at least one of gases temperature, humidity, or flow rate.

In some such configurations, additional sensors are in fluid communication with the gases passageway.

In some such configurations, the target gas characteristic or substance is a temperature level or a humidity level.

In some such configurations, the controller is mounted or connected to a housing that envelopes the first compartment and the second compartment.

In some such configurations, the controller is associated with one of the first compartment and the second compartment.

In some such configurations, the controller is adapted to control the humidification arrangement.

In some such configurations, the controller is adapted to vary an output of a heater.

In some such configurations, the controller is adapted to control an actuator that varies an exposed surface area of a reservoir. In some such configurations, the actuator is adapted to move a partition or panel.

In some such configurations, the controller is adapted to vary a flow path through the humidification arrangement by controlling one or more valves within the humidification arrangement.

In some configurations, a multiple stage respiratory gases conditioning system comprises the arrangement of any of the above, wherein the controller is adapted to receive data from the sensor; determine a control strategy as a function of the data received from the sensor and a target gas characteristic or substance being delivered by the system; and control a level of the gas characteristic or substance generated by each of the multiple stages based upon the determined control strategy.

In some such configurations, the controller is further adapted to control an amount of moisture contributed to the multiple stage respiratory gases conditioning system by a stage of the multiple stages by varying a heater output for that stage.

In some such configurations, the controller is further adapted to control an amount of moisture contributed to the multiple stage respiratory gases conditioning system by a stage of the multiple stages by varying a contact surface area of the water reservoir within that stage.

In some such configurations, the controller is further adapted to control whether a stage of the multiple stages contributes moisture to the multiple state respiratory gases condition system by altering the gases pathway through the multiple stage respiratory gases conditioning system.

In some such configurations, the controller is further adapted to control whether a stage of the multiple stages contributes moisture by bypassing or passing gases through that stage.

In some such configurations, the controller is further adapted to determine a common control strategy for all stages of the multiple stage respiratory gases conditioning system.

In some such configurations, the controller is further adapted to determine independent control strategies for each of the stages.

In some such configurations, the controller is further adapted to determine a control strategy based upon a target gas characteristic or substance specific to a stage of the multiple stages.

In some such configurations, the controller is further adapted to use a stage target that represents a desired amount to increase the gas characteristic or substance for the gases flowing through that stage.

In some such configurations, the controller is further adapted to use a target gas characteristic or substance that is a target temperature level or a target humidity level.

In some such configurations, the controller is further adapted to use sensor data that represents at least one of a temperature level, a humidity level, and a flow rate.

In some such configurations, the controller is further adapted to use sensor data that is measured at an inlet to the system.

In some such configurations, the controller is further adapted to use sensor data that is measured at an outlet from the system.

Additionally, in accordance with certain features, aspects and advantages of at least one of the embodiments disclosed herein, a gas delivery system is disclosed. The gas delivery system may comprise a flow generator and at least one of the humidification arrangements mentioned above.

BRIEF DESCRIPTION OF THE DRAWINGS

Specific embodiments and modifications thereof will become apparent to those skilled in the art from the detailed description herein having reference to the figures that follow.

DETAILED DESCRIPTION

Figure 1:
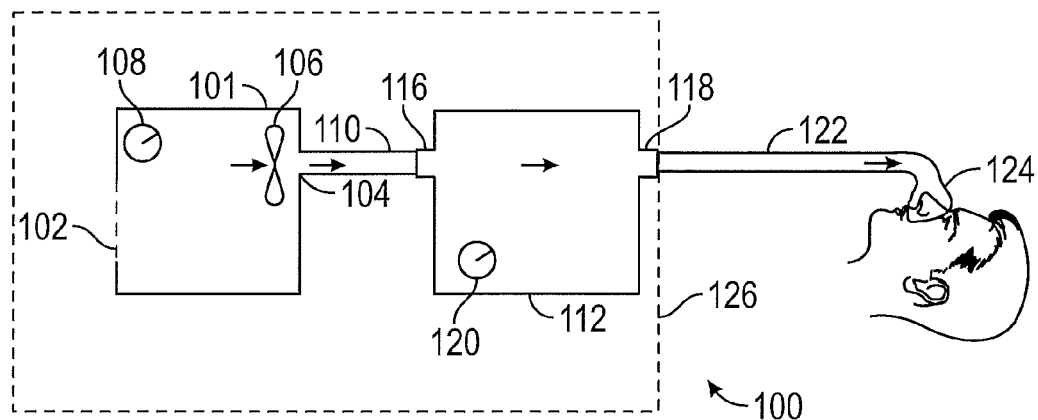
FIG. 1 shows a schematic diagram of a respiratory therapy system.

With reference to FIG. 1, a configuration for a respiratory therapy system 100 is shown. In the illustrated configuration, the respiratory therapy system 100 may comprise a flow generator 101.

The flow generator 101 may comprise a gas inlet 102 and a gas outlet 104. The flow generator 101 may comprise a blower 106. The blower 106 may comprise a motor. The motor may comprise a stator and a rotor. The rotor may comprise a shaft. An impeller may be linked to the shaft. In use, the impeller may rotate concurrently with the shaft to draw in gas from the gas inlet 102.

The flow generator 101 may comprise a user control interface 108 that may comprise one or more buttons, knobs, dials, switches, levers, touch screens, speakers, displays, and/or other input or output modules that a user might use to input commands into the flow generator 101 to view data and/or control its operation and/or the operation of other aspects of the respiratory therapy system 100.

The flow generator 101 may pass gas through the gas outlet 104 to a first conduit 110. The first conduit 110 may pass gas to a humidification arrangement 112 that may be used to entrain moisture in the gas in order to provide a humidified gas stream. The humidification arrangement 112 may comprise a humidification inlet 116 and a humidification outlet 118. The humidification arrangement 112 may comprise water or another moisturizing agent (hereinafter referred to as water).

The humidification arrangement 112 may also comprise a heating arrangement that may be used to heat the water in the humidification arrangement 112 to encourage water vaporization and/or entrainment in the gas flow and/or increase the temperature of gases passing through the humidification arrangement 112. The heating arrangement may, for example, comprise a resistive metallic heating plate.

The humidification arrangement 112 may comprise a user control interface 120 that may comprise one or more buttons, knobs, dials, switches, levers, touch screens, speakers, displays and/or other input or output modules that a user might use to input commands into the humidification arrangement 112 to view data and/or control its operation and/or the operation of other aspects of the respiratory therapy system 100.

Additional configurations of the humidification arrangement 112 are described elsewhere in this disclosure and in the accompanying figures.

Gas may pass from the humidification outlet 118 to a second conduit 122. The second conduit 122 may comprise a conduit heater. The conduit heater may be used to add heat to gases passing through the second conduit 122. The heat may reduce or eliminate the likelihood of condensation of water entrained in the gas stream along a wall of the second conduit 122. The conduit heating arrangement may comprise one or more resistive wires located in, on, around or near a wall of the second conduit 122.

Gas passing through the second conduit 122 may then enter a patient interface 124 that may pneumatically link the respiratory therapy system 100 to an airway of a patient. The patient interface 124 may comprise a sealing or non-sealing interface, and may comprise a nasal mask, an oral mask, an oro-nasal mask, a full face mask, a nasal pillows mask, a nasal cannula, an endotracheal tube, a combination of the above or some other gas conveying system.

In the illustrated configuration, and as implied above, the respiratory therapy system 100 may operate as follows. Gas may be drawn into the flow generator 101 through the gas inlet 102 due to the rotation of an impeller of the motor of the blower 106. The gas may then be propelled out of the gas outlet 104 and along the first conduit 110. The gas may enter the humidification arrangement 112 through the humidification inlet 116. Once in the humidification arrangement 112, the gas may entrain moisture when passing over or near water in the humidification arrangement 112. The water may be heated by the heating arrangement, which may aid in the humidification and/or heating of the gas passing through the humidification arrangement 112. The gas may leave the humidification arrangement 112 through the humidification outlet 118 and enter the second conduit 122. Gas may be passed from the second conduit 122 to the patient interface 124, where the gas may be taken into the patient's airways to aid in the treatment of respiratory disorders.

The illustrated configuration should not be taken to be limiting. Many other configurations for the respiratory therapy system 100 are possible. In some configurations, the flow generator 101 may, for example, comprise a source or container of compressed gas (for example, air, oxygen, etc.). The flow generator 101 may comprise a valve that may be adjusted to control the flow of gas leaving the container. In some configurations, the flow generator 101 may use such a source of compressed gas and/or another gas source in lieu of the blower 106. In some configurations, the blower 106 may be used in conjunction with another gas source. In some configurations, the blower 106 may comprise a motorized blower or may comprise a bellows arrangement or some other structure capable of generating a gas flow. In some configurations, the flow generator 101 may draw in atmospheric gases through the gas inlet 102. In some configurations, the flow generator 101 may be adapted to both draw in atmospheric gases through the gas inlet 102 and accept other gases (for example, oxygen, nitric oxide, carbon dioxide, etc) through the same gas inlet 102 or a different gas inlet. In some configurations, the flow generator 101 and the humidification arrangement 112 may share a single housing 126.

In some configurations, the respiratory therapy system 100 may comprise a single user interface located on the first flow generator 101, the humidification arrangement 112, the first 110 or second conduit 122, the patient interface 124, or another component of the respiratory therapy system 100. In some configurations, the operation of components of the respiratory therapy system 100 may be actuated wirelessly using a user interface located on a remote computing device, which may be a tablet, a mobile phone, a personal digital assistant, or another computing device. In some configurations, the operation of the flow generator 101, of the humidification arrangement 112, or of other components or aspects of the respiratory therapy system 100 may be controlled by a controller. The controller may comprise a microprocessor. The controller may be located in or on the flow generator 101, the humidification arrangement 112, or other components of the respiratory therapy system 100 or on a remote computing device. In some configurations, multiple controllers may be used.

In some configurations, the respiratory therapy system 100 may comprise one or more sensors for detecting various characteristics of gases in the respiratory therapy system 100, including pressure, flow rate, temperature, absolute humidity, relative humidity, enthalpy, gas composition, oxygen concentration, and/or carbon dioxide concentration, one or more sensors for detecting various characteristics of the patient or of the health of the patient, including heart rate, EEG signal, EKG/ECG signal, blood oxygen concentration, blood $CO_2$ concentration, and blood glucose, and/or one or more sensors for detecting various characteristics of gases or other objects outside the respiratory therapy system 100, including ambient temperature and/or ambient humidity. One or more of the sensors may be used to aid in the control of components of the respiratory therapy system 100, including the humidification arrangement 112, through the use of a closed or open loop control system.

In some configurations, there may be no user control interface or a minimal user control interface for components of the respiratory therapy system 100. In some such configurations, the respiratory therapy system 100 may utilize a sensor to determine if the patient is attempting to use the respiratory therapy system 100 and automatically operate (for example, the flow generator 101 may generate a gas flow, the humidification arrangement 112 may humidify gases, etc) according to one or more predetermined parameters if data obtained from the sensor indicates that the patient is attempting to use the respiratory therapy system 100. In some configurations, the respiratory therapy system 100 may utilize a two-limb system comprising separate inspiratory and expiratory gas passageways that may interface with one or more airways of the patient.

Many configurations of the respiratory therapy system 100 may also be used for other applications not involving providing gases to an airway of a patient. For example, the respiratory therapy system 100 could instead be used for providing an insufflation gas in laparoscopic surgery. This may be enacted, for example, by replacing the interface 124 with a surgical cannula that may be inserted into an abdominal cavity that has been punctured with a trocar.

Figure 2:
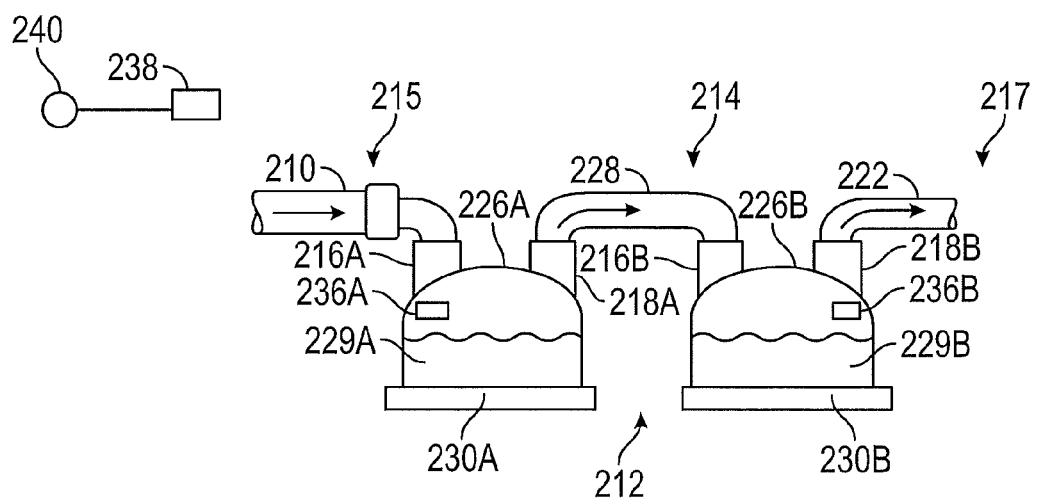
FIG. 2 shows a configuration for a humidification system.

FIG. 2 presents a humidification arrangement 212 demonstrating certain features, aspects and advantages of the present disclosure. The humidification arrangement 212 may comprise a gas passageway 214 that may comprise a first location 215 representing a point at which gases enter the humidification arrangement 212 or a point at which the gases passing through the humidification arrangement 212 originate, and a second location 217 representing a point at which gases leave the humidification arrangement 212. For example, the first location 215 may be at a point along a first conduit 210 that delivers gases to the humidification arrangement 212, or at a first humidification inlet 216A, and the second location 217 may be at a point along a second conduit 222 that receives gases from the humidification arrangement 212, or at the second humidification outlet 218B. The gas passageway 214 may be defined, at least in part, as the path taken by gases passing through the humidification arrangement 212 between the first and second locations 215, 217. Preferably, the gas passageway 214 is substantially isolated from the environment outside of the humidification arrangement 212 (for example, the ambient environment).

The gas passageway 214 may comprise a first compartment 226A and a second compartment 226B. The word 'compartment' in this disclosure is not necessarily intended to mean a part, section, or region of a larger device or apparatus, as demonstrated in the accompanying disclosure and figures. The first and second compartments 226A, 226B may be configured to add moisture to gases passing through the gas passageway 214. The first compartment 226A may comprise a first moisture source 229A.

The first moisture source 229A may comprise a volume of water that may help to add moisture to gases passing over the volume of water (for example, via pass-over humidification). Various configurations for the first moisture source 229A are possible. For example, the first moisture source 229A may comprise a hydrophilic material or sponge at least partially imbued with water. The hydrophilic material may comprise natural or artificial sponge, melamine foam, metal (for example, sodium) polyacrylates, calcium chloride, or other materials exhibiting a relatively high capacity for retaining moisture. The first moisture source 229A could comprise reagents for forming water chemically, which could be mixed in controlled amounts to produce water available for gas moisturization.

The moisture output of the first moisture source 229A may be adjustable. 'Moisture output' in some contexts may refer to the ability of the moisture source of a compartment to provide moisture to a gas flow. For example, the first moisture source 229A may comprise a first heater 230A that may be adjusted to help in controlling the moisture output of the first moisture source 229A. The heat output of the first heater 230A may be adjustable. 'Heat output' in some contexts may refer to the ability of a heater to provide heat to a moisture source, which may in turn affect the moisture output of the moisture source. The first heater 230A may comprise a resistive heating element that may be placed near the first moisture source 229A.

Various configurations for the first heater 230A are possible. For example, the first heater 230A may comprise a chemical heater capable of utilizing controlled exothermic reactions to transfer heat to the first moisture source 229A. Similarly, the second compartment 226B may comprise a second moisture source 229B and may comprise a second heater 230B, and similarly, the moisture output of the second moisture source 229B may be adjustable.

The second compartment 226B may be downstream of the first compartment 226A. 'Downstream' in this context may mean that the second compartment 226B is 'further along' the gas passageway than the first compartment 226A, or that, in use, gases passing through the humidification arrangement 212 may pass through the first compartment 226A before passing through the second compartment 226B. A tube section or passage 228 may link the first and second compartments 226A, 226B. The tube section or passage 228 may provide a pathway for pneumatic communication between the first and second compartments 226A, 226B. The tube section 228 may comprise a tube heater. The tube heater may add heat to gases passing between the first and second compartments 226A, 226B. This heat may help to reduce the condensation of moisture along the walls of the tube section 228.

The humidification arrangement 212 may comprise a system controller 238 configured to control the operation of components of the humidification arrangement 212. The system controller 238 may receive an input signal from one or more sensor modules 240 located in and/or outside the humidification arrangement 212 or a respiratory therapy system connected to the humidification arrangement 212. For example, one or more of the sensor modules 240 may be positioned in a gases conduit (for example, the second conduit 122 described elsewhere in this disclosure with reference to FIG. 1) or a patient interface (for example, the patient interface 124 described elsewhere in this disclosure with reference to FIG. 1). One or more of the sensor modules 240 may include, for example, an ambient temperature sensor, an ambient humidity sensor, a flow sensor, a pressure sensor, and/or some other sensor. The controller 238 may use the input signal from the one or more sensor modules 240 to aid in the control of the humidification arrangement 212, the first compartment 226A, and/or the second compartment 226B. In some configurations, multiple sensor modules 240 may be utilized. The sensor modules 240 may be located in the same place or in different places around the humidification arrangement 212 or respiratory therapy system as mentioned above. In some configurations, the first compartment 226A may comprise a first compartment controller 236A that may help to control the operation of the first compartment 226A. The first compartment controller 236A may communicate with the system controller 238, the sensor module 240, or a second compartment controller 236B. Similarly, the second compartment 226B may comprise a second compartment controller 236B that may help to control the operation of the second compartment 226B.

The humidification arrangement 212 of FIG. 2 may operate as follows. Gases may pass through the first conduit 210 (which may comprise the first location 215 of the gas passageway 214), through the first humidification inlet 216A, and into the first compartment 226A. The gases may be humidified through interaction with the first moisture source 229A, which may be heated by the first heater 230A. The gases may then continue through the first humidification outlet 218A, through the tube section 228 (which may heated by a tube heater), through the second humidification inlet 218B, and into the second compartment 226B. Gases may be further humidified through interaction with the second moisture source 229B, which may be heated by the second heater 230B. Gases may then continue through the second humidification outlet 218B and through the second conduit 222 (which may comprise the second location of the gas passageway).

The operation of components of the humidification arrangement 212 may be controlled by the system controller 238, the first compartment controller 236A, and/or the second compartment controller 236B, and any or each of the controllers 238, 236A, 236B may receive input signals from one or more sensors as described above, which may be utilized in closed or open loop control of the moisture outputs of the compartments and/or heat outputs of the heaters of the compartments.

Advantageously, by utilizing multiple compartments with separate moisture sources (relative to a single compartment with a relatively more voluminous moisture source), the total contact surface area of the moisture sources with a stream of gas passing through the humidification arrangement 212 may be relatively large, which may help to improve the moisture output for the humidification arrangement 212, which may be helpful for relatively large gas flow rates (for example, 80 L/min of gas or higher). Heaters used with the moisture sources can be relatively less powerful due to the less voluminous (and less massive) moisture source, which can help in achieving a desired level of stability in the moisture output of the humidification arrangement 212, which may be helpful for relatively small gas flow rates (for example, 20 L/min of gas or lower).

The moisture output of the first moisture source 229A (and/or the heat output of the first heater 230A) and the moisture output of the second moisture source 229B (and/or the heat output of the second heater 230B) may be controlled using a single set of input conditions. For example, the first and second moisture sources 229A, 229B may be controlled such that the moisture output of each of the first and second moisture sources 229A, 229B is set to a function of one or more set points defining desired characteristics of the gas downstream of the humidification arrangement 212. The set points may be entered by a patient or other user of the humidification arrangement 212 using a user interface located on or near the humidification arrangement 212 or elsewhere as described above. The set points could be, for example, a desired absolute humidity and/or temperature of gases exiting the humidification arrangement 212, of gases entering the patient interface, or of gases entering an airway of a patient.

The input conditions may include signals from various sensors as noted above (which may be placed, for example, at the end of the humidification arrangement 212, in the patient interface, or elsewhere). For example, the moisture output of each of the first and second moisture sources 229A, 229B may be set to a function of an output signal of a flow sensor (for example, adapted to measure the flow rate of gases entering the humidification arrangement 212), an ambient temperature sensor and/or an ambient humidity sensor. Synchronizing the moisture outputs of the first and second moisture sources 229A, 229B (and/or the heat outputs of the first and second heaters 230A, 230B) according to the same set of input conditions may help to improve the output stability (for example, in relation to delivering gases with given set points under varying flow conditions) of the humidification arrangement 212.

In some configurations, the humidification arrangements 212 may be configured to deliver hyperthermic gases (for example, deliver gases at higher temperatures than a patient's body temperature) to a patient with a relatively high level of output stability for a range of possible flow rates. The hyperthermic gases may be in the range of, for example, 37-48 degrees Celsius or any desired subrange defined within that range. Hyperthermic gases may, for example, help to alleviate the symptoms of bacterial and/or viral infections by attenuating or killing or preventing replication of bacteria or viruses residing the airways of a patient. In some cases, hyperthermic gases may induce cytospecific DNA damage in tumor cells. In other words, hyperthermic gas therapy may be useful for treating some cancers of the respiratory airways, which may proceed by, for example, triggering cancer cell apoptosis or promoting the thermolysis of cancer cells. Hyperthermic therapy modes may be defined that may be activated and/or deactivated manually and/or automatically at predetermined times during a therapy session.

It should be understood that many variations of the humidification arrangement 212 are possible. For example, each compartment may comprise more than one moisture source or more than one heater. Additionally, more than two compartments may be used. For example, a third compartment comprising a third moisture source and a third heater may be connected in-line between the second compartment 226B and the second conduit 222.

In some configurations, one or more of the sensor modules 240 or one or more other sensors or sensing arrangements (including but not limited to capacitive water level sensing arrangements) may be used to determine the presence or absence of water in a given stage or compartment of the humidification arrangement 212. For example, if the humidification arrangement 212 comprises first, second and third compartments 226A, 226B, 226C, a signal may be generated by one or more of the sensors if the second compartment 226B is determined to not comprise water. In some such configurations, the humidification arrangement 212 may be arranged (for example, using a number of structures including but not limited to valves and valve arrangements) such that certain stages or compartments are bypassed dependent on the determination of 'water out' signals. As in the above example, if the second compartment 226B is determined to not comprise water, the humidification arrangement 212 may be configured such that gas flow is not permitted to pass through the second compartment 226B. Gas flow may be, for example, only permitted to pass through the first compartment 226A, the third compartment 226C, or a combination of the first and third compartments 226A, 226C, dependent on various needs or desired output gas parameters including but not limited to the desired output gas humidity.

Figure 3:
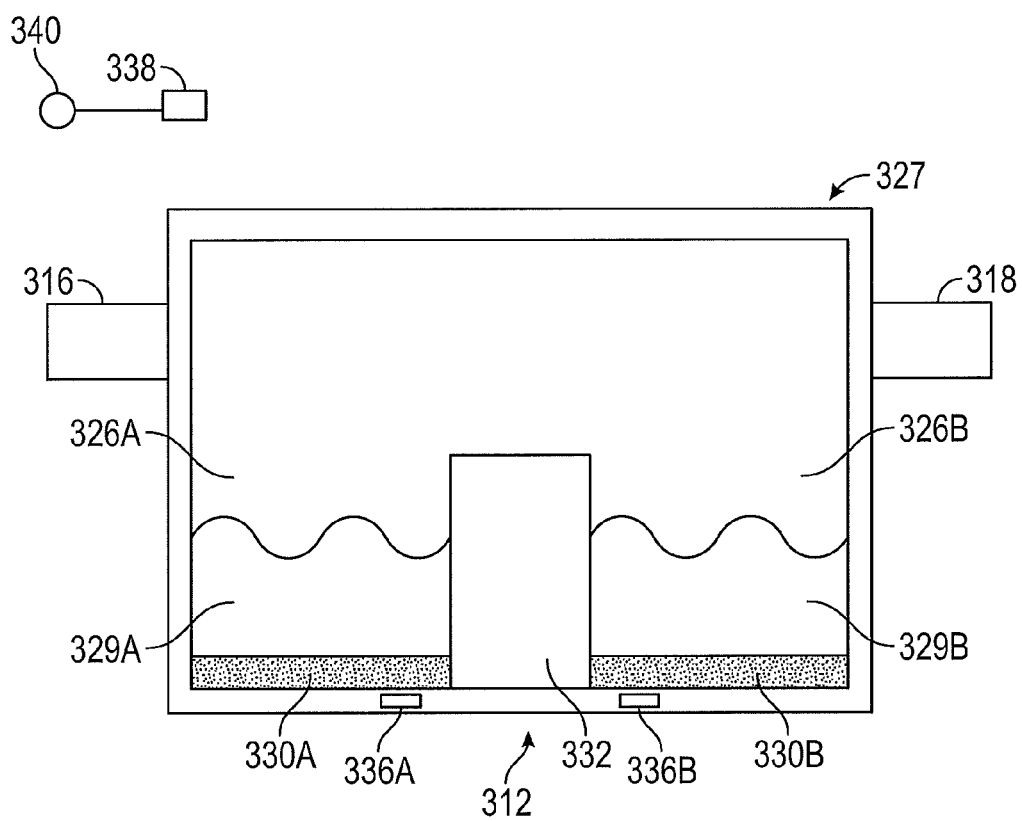
FIG. 3 shows a configuration for a humidification system.

Although FIG. 2 demonstrates that the first and second compartments 226A, 226B may be physically disparate (for example, in different housings), other configurations may be envisioned. FIG. 3 demonstrates a humidification arrangement 312 similar to the humidification arrangement 212 of FIG. 2, wherein the first and second compartments 326A, 326B are contained within a single housing 327 (in contrast to the separate and distinct first and second compartments 226A, 226B demonstrated in FIG. 2). As shown, a partition 332 may be used to separate the first and second compartments 326A, 326B. The partition 332 may comprise a thermally insulating material and/or may help to thermally isolate the first compartment 326A from the second compartment 326B such that finer control of the moisture outputs of the first and second moisture sources 329A, 329B may be achieved. The partition 332 may separate the water-containing regions, the gases-containing regions or at least a portion of both. The reference numerals used for FIG. 3 are analogous to those used for FIGS. 1 and 2, and many of the configurations mentioned in the passages above or elsewhere in this disclosure may similarly be applied to the configuration illustrated in FIG. 3.

With reference now to FIGS. 6-9, another multiple stage humidification arrangement 412 is illustrated. In the illustrated configuration, a gas passageway 414 is defined within a housing 427. As will be explained, however, the gas passageway 414 can take different paths depending upon the configuration of valves 420A, 420B, 420C, 420D.

Figure 6:
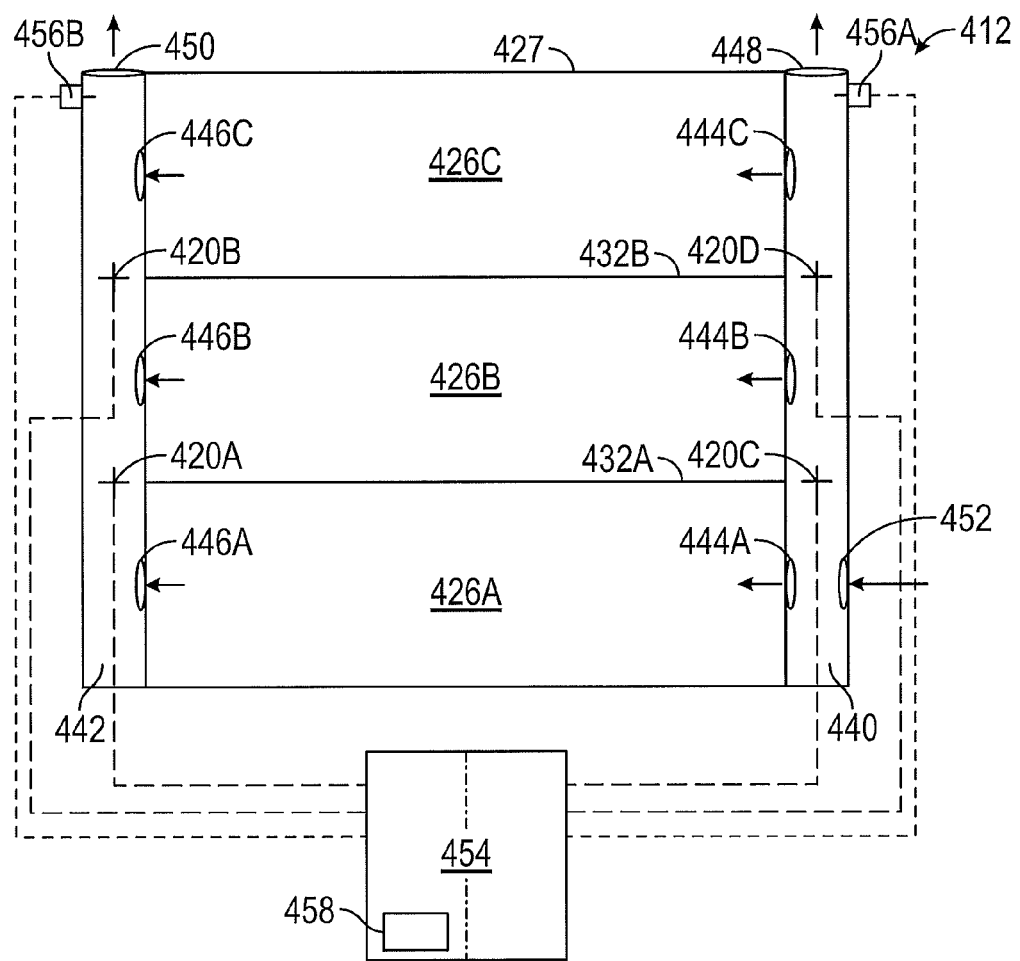
FIG. 6 shows a schematic top view of a humidification system.
Figure 7:
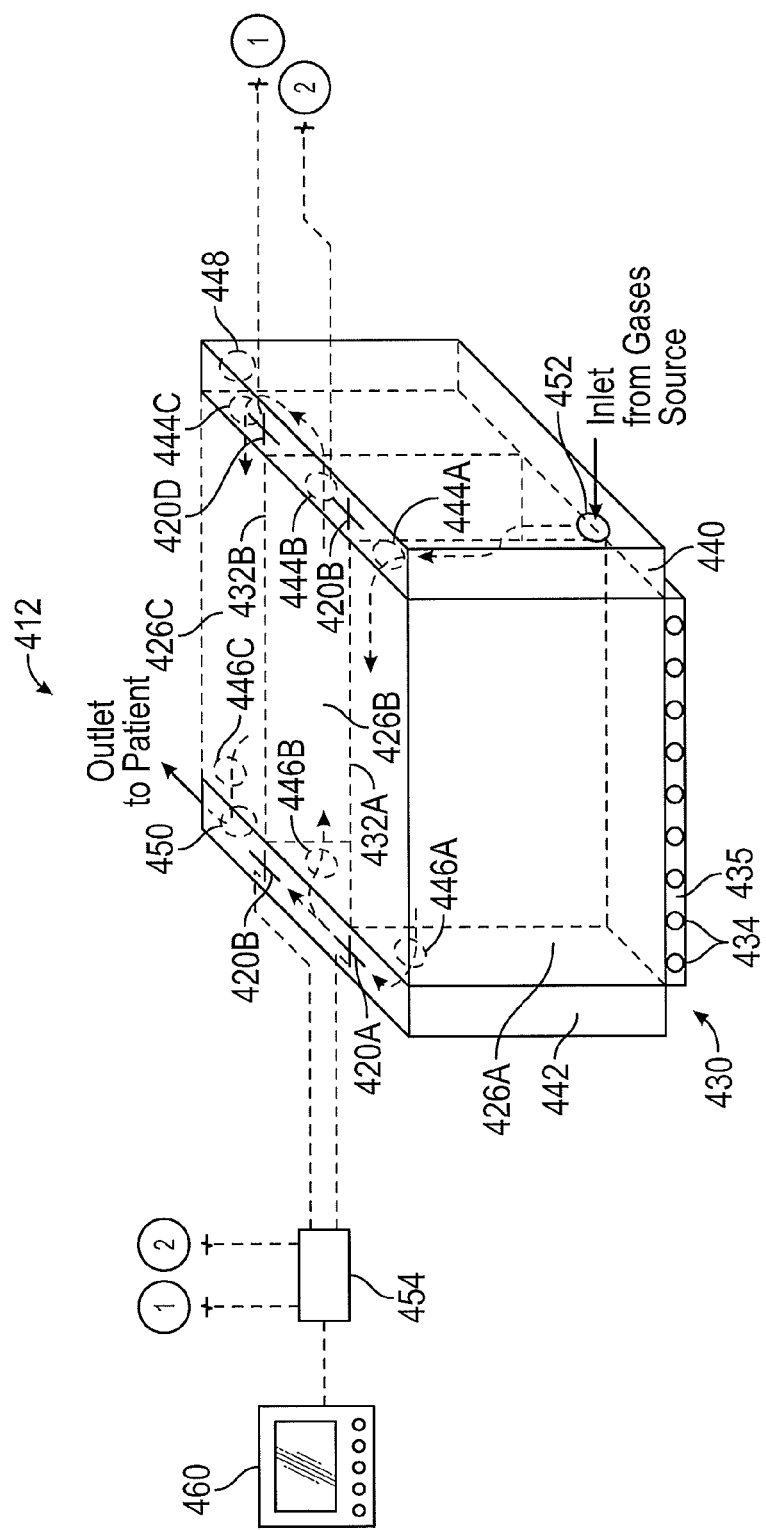
FIG. 7 shows a schematic perspective view of the humidification system of FIG. 6.

Within the housing 427 can be defined multiple stages. For example, as shown in FIG. 6, a first compartment 426A, a second compartment 426B. and a third compartment 426C all can be defined within the housing 427. In some configurations, as described above, the compartments can be formed in separate and distinct housings. In the illustrated configuration of FIG. 6, however, a first partition 432A can separate the first compartment 426A from the second compartment 426B and a second partition 432B can separate the second compartment 426B from the third compartment 426C. The partitions 432A, 432B can completely separate the compartments 426A, 426B, 426C. In some configurations, one or both of the partitions 432A, 432B only partially separate the respective compartments 426A, 426B, 426C. In some configurations, the partitions 432A, 432B are thermally isolating such that heat transfer between the compartments is less likely. Any number of stages or compartments might be created, not just three. For example, 2, 4, 5 or more stages might be used. The humidification arrangement 412 might be sufficiently modular that, if more stages are engaged or joined, the control strategy might be updated to utilize those stages to improve output stability/resolution.

Each of the first compartment 426A, the second compartment 426B, and the third compartment 426C can be configured to contain a body of water. In some configurations, the body of water contained in the first compartment 426A is isolated from the body of water contained in the second compartment 426B and the body of water contained in the third compartment 426C. In some configurations, the body of water contained in the second compartment 426B is isolated from the body of water contained in the third compartment 426C.

In some configurations, as described above, the water may not necessarily be contained in a body or pool of water. In some configurations, the water may be contained within a sponge-like adsorbent material that releases the water into the gases passing over the material. In some configurations, the adsorbent material might be present just on the base of the compartment. In some configurations, the adsorbent material may be present on one or more of the base, the sides or the top of the compartment. In some configurations, a heater or the like can be used to supply a temperature increase or gradient to at least a portion of the adsorbent material to improve the moisture output from the adsorbent material. For example, the heater or the like can be connected to, positioned adjacent to or embedded within the adsorbent material.

In some configurations, the moisture output is controllable within one or more of the compartments 426A, 426B, 426C without the use of temperature changes (for example, heating) associated with any component of the compartment 426A, 426B, 426C. In some such configurations, the adsorbent material may be sponge-like and may incorporate a piezoelectric material (for example, ferroelectric ceramic-polymer composites) such that the adsorbent material becomes more or less porous upon the application of electrical energy. In such a manner, the adsorbent material can have a variable effective exposed surface area of water in the material, thereby the exposed surface area can be modulated. In some configurations, at least a portion of at least one of the chambers 426A, 426B, 426C can incorporate surface structures or coatings that can draw liquid upward from a pool of liquid. In such configurations, the exposed surface area can be increased to increase the transfer of moisture into the gases flow. For example, the sides and/or the top of the chamber can be provided with microchannels such that the water moves with the assistance of capillary forces, such as described within WO2014/142677, which is hereby incorporated by reference in its entirety). In some configurations, the microchannels or other surface texture can be constructed from piezoelectric materials (e.g., ferroelectric ceramic-polymer composites) that expand or contract upon application of electrical energy. Such a configuration can advantageously be used to control or modulate the rate of water transfer along the microchannels.

The compartments 426A, 426B, 426C can be heated in any suitable manner. One or more heaters 430 can be used. In some configurations, the heaters can use heat transferred from hot fluid (for example, hot water) that is pumped through passages 434 formed in a base 435 of the humidification arrangement 412. In the illustrated configuration, one or more of the passages 434 spans two or more compartments 426A, 426B, 426C. In some configurations, one or more passages 434 span all three compartments 426A, 426B, 426C. Such configurations are more likely to provide consistent heat transfer to each of the three compartments 426A, 426B, 426C. Alternatively, one or more passages 434 can be configured to pass only within one of the three compartments 426A, 426B, 426C. Such a configuration can facilitate differential levels of heat transfer among the compartments 426A, 426B, 426C.

In the illustrated configuration, heated water is used to heat water contained within the compartments 426A, 426B, 426C. Other mechanisms for heating the water contained within the compartments 426A, 426B, 426C also can be used. For example, one or more resistive heating elements can be used to heat each or all of the compartments 426A, 426B, 426C. In some such configurations, the resistive heating elements can be metallic in nature. In some configurations, the heater 430 can be one or more chemical heaters. In some configurations, the heater 430 can be distinct heating elements used for at least a portion of only a single chamber and the distinct heating elements can be separately controllable.

Figure 8:
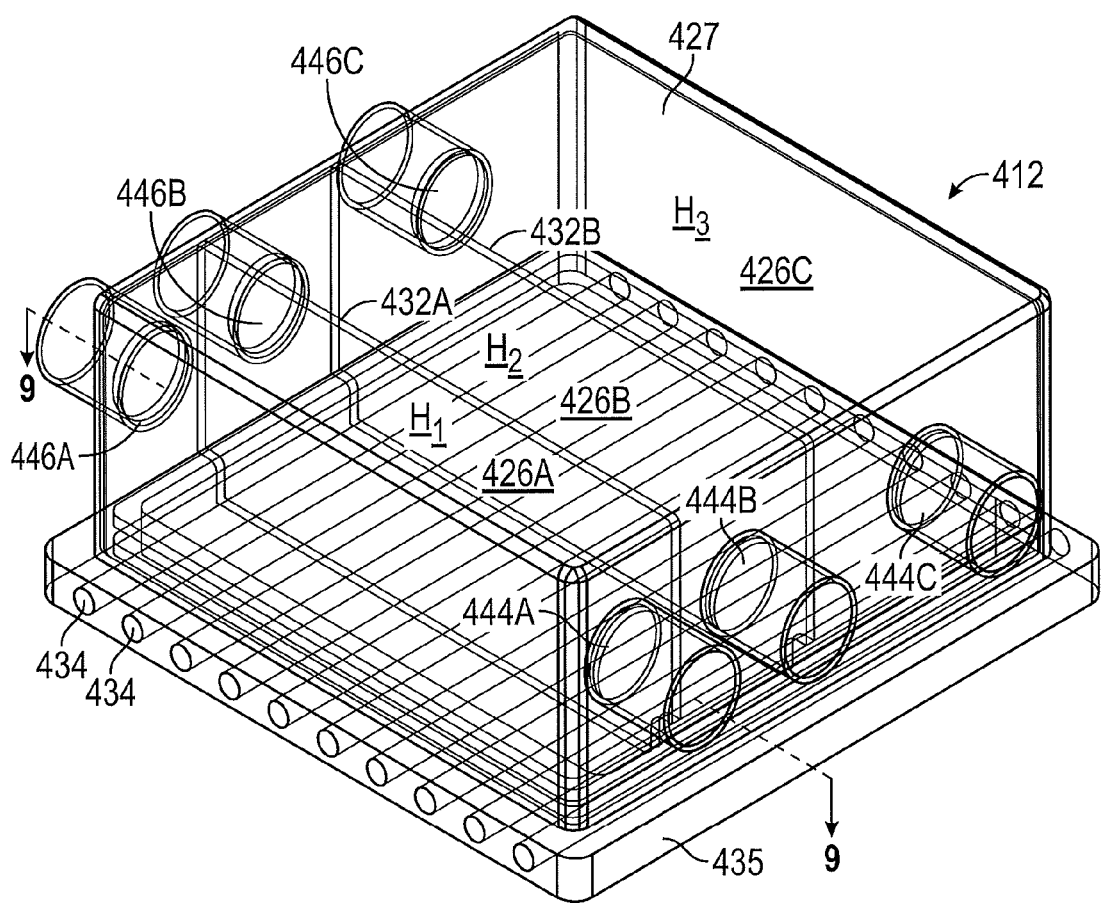
FIG. 8 shows a perspective view of a portion of a humidification system similar to the humidification system of FIG. 6 but with differently sized compartments.
Figure 9:
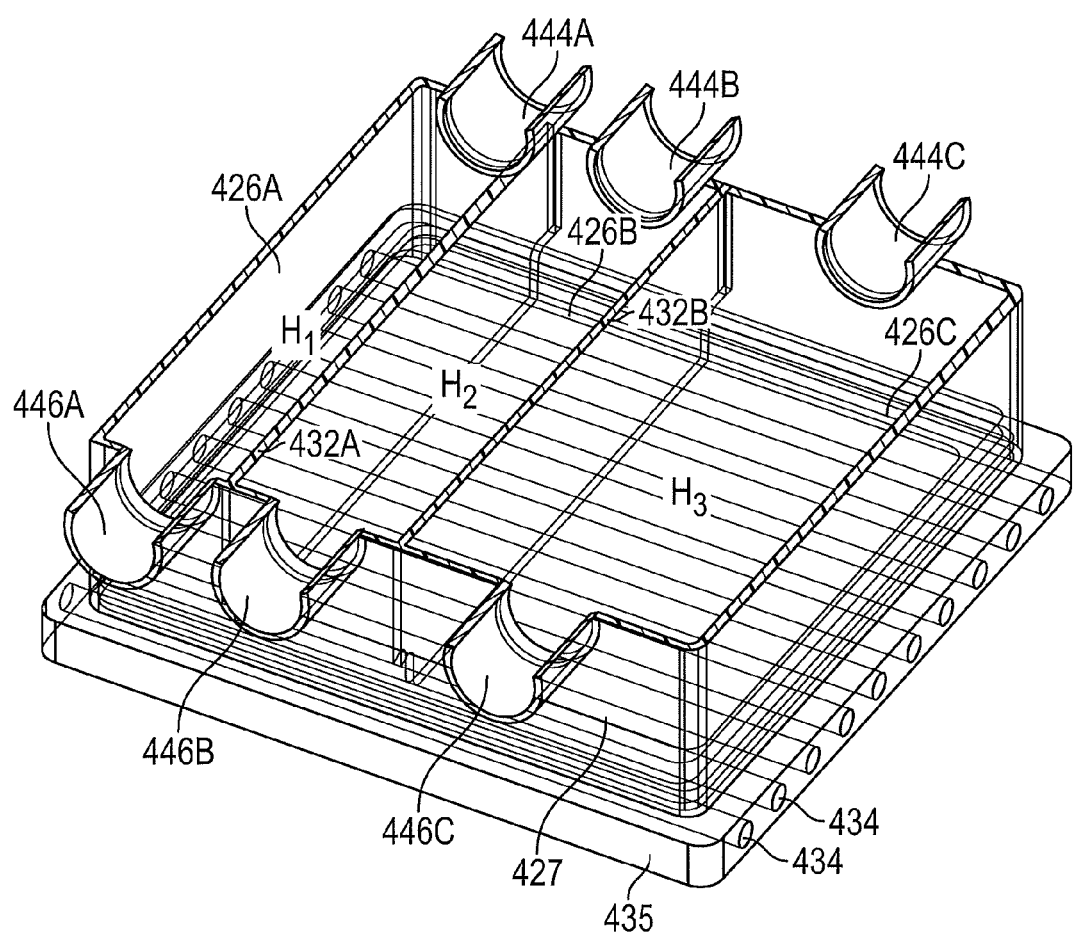
FIG. 9 is a sectioned view of the portion of FIG. 8 taken along the line 9-9.

With continued reference to FIG. 6, the compartments 426A, 426B, 426C can be interconnected in any suitable manner. In the illustrated configuration, a first manifold 440 and a second manifold 442 can be used to connect the compartments 426A, 426B, 426C. The first manifold 440 is connected to a first end of each of the compartments 426A, 426B, 426C while the second manifold 442 is connected to a second end of the compartments 426A, 426B, 426C. A first set of passages 444A, 444B, 444C connects a lumen or inner passageway of the first manifold 440 with the respective compartments 426A, 426B, 426C. A second set of passages 446A, 446B, 446C connects a lumen or inner passageway of the second manifold 442 with the respective compartments 426A, 426B, 426C. As shown in FIGS. 8 and 9, the passages 444A, 444B, 444C, 446A, 446B, 446C can be formed of tubular members or the like. The first manifold 440 also comprises an outlet 448 and the second manifold also comprises an outlet 450. Finally, the first manifold 452 comprises an inlet 452.

In some configurations, flow may be desired through less than all of the compartments 426A, 426B, 426C. In such configurations, valves 420A, 420B, 420C, 420D can be disposed within the first and second manifolds 440, 442. The valves 420A, 420B, 420C, 420D can be any suitable type of valves. In some configurations, the valves 420A, 420B, 420C, 420D can be electro-mechanical valves. In such configurations, a controller 454 can be operatively connected to the valves 420A, 420B, 420C, 420D. The connections can be physical (for example, with wires) or can be wireless. The controller 454 can cause the valves 420A, 420B, 420C, 420D to be in a first or opened position or in a second or closed position. In some configurations, a separate controller 454 can be used for each of the manifolds 440, 442 (as represented by the dashed line in FIG. 6). In some configurations, each compartment 426A, 426B, 426C could have a separate controller 454.

In some configurations, the controller 454 can be connected to one or more sensors 456A, 456B, 458. In some such configurations, one or more of the sensors 456A. 456B, 458 can be a humidity sensor. As illustrated, one or more of the sensors 456A, 456B can be positioned within the first and/or second manifolds 440, 442. The sensor 456A is positioned near the outlet 448 of the first manifold 440 and the sensor 456B is positioned near the outlet 450 of the second manifold 442. An atmospheric condition sensor 458 can be positioned to detect one or more property of the ambient conditions (for example, humidity, temperature, flow rate). Any one or more of these sensors 456A, 456B, 458 can be omitted. In some such configurations, sensors can be positioned in multiple locations along the associated manifold 440, 442. In some such configurations, a separate controller 454 can be associated with each compartment 426A, 426B, 426C and a determination of whether to open the compartment to flow can be made based upon a comparison between a set point for humidity level and a sensed humidity level.

The compartments 426A, 426B, 426C and the partitions 432A, 432B can be arranged such that humidity outputs or humidity contributions to the gas flowing through the humidification arrangement 412 can be additive. In some configurations, the compartments 426A, 426B, 426C and the partitions 432A, 432B are configured such that H1<H2<H3 (for example, the maximum contribution of humidity H1 is less than the maximum contribution of humidity H2, and so on). In some configurations, the compartments 426A, 426B, 426C are configured such that H1=H2=H3 (for example, the maximum contribution of humidity H1 is generally the same as H2, and so on).

Output of the sensors 456A, 456B, 458 can be used to determine the humidity of the flow and a humidity set point can be determined. In some configurations, the humidity set point can be provided by using a control interface 460. The control interface 460 can be any suitable user control interface and can include displays and input elements (for example, touch screens, buttons, knobs, or the like). With the set point and the sensed current humidity contributed to the gas flow, the humidification arrangement 412 can be configured to manage the total humidity contribution to the gas flow passing through the humidification arrangement 412.

In some configurations, the humidification arrangement 412 controls the humidity contribution by controlling a flow path through the humidification arrangement 412. In some such configurations, the controller 454 can open and close one or more of the valves 420A, 420B, 420C, 420D. For example, if the amount of humidity sought to be added to the gas flow is low, the flow can be configured to pass through only one of the compartments 426A, 426B, 426C. In other words, the valve 420A and the valve 420B can be used to direct flow from the first chamber 426A to the outlet 450 while diverting the flow from the chambers 426B, 426C. In addition, the valve 420B can ensure that all of the flow passes into the first chamber 426A. To provide a higher level of humidity to the gas flow, the flow can be directed through the first chamber 426A and the second chamber 426B. To provide a yet higher level of humidity to the gas flow, the flow can be directed through the first chamber 426A, the second chamber 426B, and the third chamber 426C. In short, the humidity or moisture contributed to the gas flow is a function of the total surface area of the water in the reservoirs exposed to the gas flow and that total surface area can be varied by diverting the flow.

With reference again to FIGS. 6-9, in the illustrated configuration, there are six distinct options for moving the gas flow through the humidification arrangement 412. Assuming that H1<H2<H3, where H1 is the maximum humidity contribution from the first chamber 426A, H2 is the maximum humidity contribution from the second chamber 426B, and H3 is the maximum humidity contribution from the third chamber 426C, then there are the follow permutations: [H1]<[H2]<[H3]<[H1+H2]<[H1+H3]<[H2+H3]<[H1+H2+H3]. In addition, it is possible to divert the gas flow away from all of the chambers 426A, 426B, 426C. In these manners, it is possible to obtain a better degree of control over the changing levels of humidity needed for changes in gas flow. In some configurations, such as those involving independently controllable heating elements and thermally isolating partitions with multiple selectable compartments or stages, the resolution of humidity variations can be vastly improved.

In some configurations, the humidification arrangement 412 can be a "gas conditioning system." In such configurations, the valves 420A, 420B, 420C, 420D and the compartments 426A, 426B, 426C can be coordinated such that a temperature set point (for example, a desired output gas temperature) can be attained. In some such configurations, H2 could mean a greater maximum heat contribution to the gas flow than H1, and so on. Such configurations can provide fine control of output gas temperature. Fine temperature control can be important in, for example, hyperthermic gas therapy, where maintaining a temperature that is high enough to kill or attenuate viruses/bacteria/cancer cells in the airway cavity while avoiding permanent damage to other cells lining the respiratory cavities is currently believed to be crucial. Similarly, the gas conditioning system might be configured to add nebulized/aerosolized medication or other substances in stages based on a dosage set point.

Figure 5:
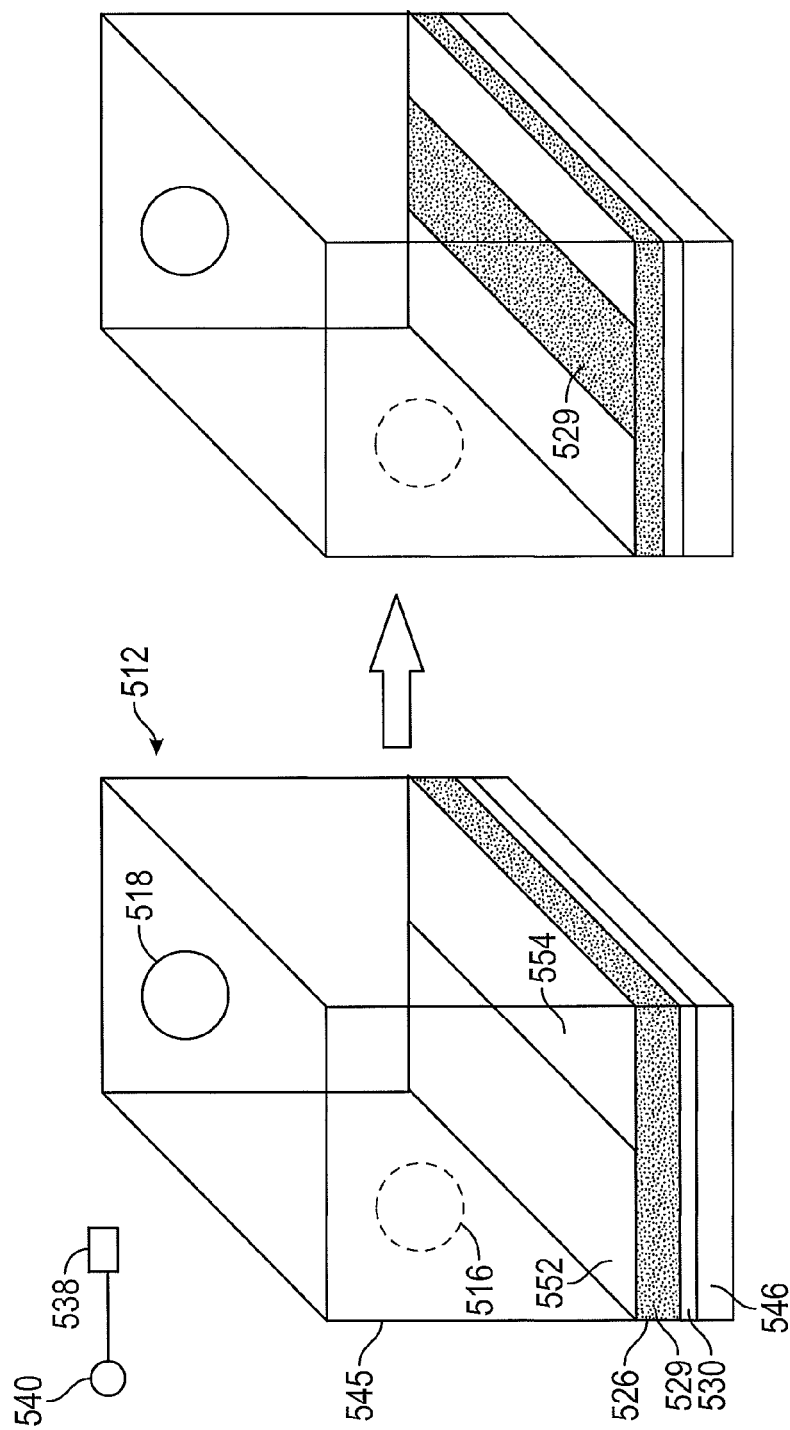
FIG. 5 shows a configuration for a humidification system.

Although some of the configurations described above show that the moisture output of a humidification arrangement may be adjusted by adjusting the heat output of heaters in the compartments of the humidification arrangement (for example, by adjusting the duty cycle of a resistive heating element adapted to heat a moisture source of a compartment, which may be a reservoir of water that gas passing through the humidification arrangement passes over), there are other ways to adjust the moisture output of a humidification arrangement. For example, as discussed above, in some configurations, the moisture output of a humidification arrangement may be adjusted by changing the surface area of the moisture source that is exposed to the gas flow passing through one or more compartments of the humidification arrangement. FIG. 5 demonstrates an exemplary humidification arrangement 512 illustrating certain features and aspects of the above concept.

The humidification arrangement 512 may comprise a wall 545, a base 546, a humidification inlet 516 and a humidification outlet 518. The humidification arrangement 512 may comprise a chamber or reservoir 529 that may comprise water. The surface of the water in the reservoir 529 may be at least partially occluded by a first panel 552 and a second panel 554. The first and second panels 552, 554 may be partially or fully electromechanically moved (for example, slid or rotated) to expose the surface of the water in the reservoir 529.

The movement of the first and second panels 552, 554 may be actuated by a controller 538 that may be in communication with a sensor module 540. The controller 538 and the sensor module 540 may be analogous to those described above in relation to FIG. 2 or 3 or those described elsewhere in this disclosure. The controller 538 may control both the first and second panels to adjust the moisture added to gases passing through the humidification arrangement 512 according to desired set points as described herein and/or according to other input signals received by a controller controlling the humidification arrangement 512.

Other moisture sources may be used in place of the reservoir 529 and multiple moisture sources and/or panels or sets of panels may be used to control the moisture output of the humidification arrangement 512. Any number of panels may be utilized. The moisture sources used may be thermally isolated from one another through the use of partitions or other isolating components.

The humidification arrangement 512 may comprise one or more heaters 530 adapted to heat the reservoir 529 and/or the other moisture sources used. The heaters 530 may comprise a positive thermal coefficient (PTC) panel comprising selectively heatable sections. The sections may be thermally isolated from one another. The heaters 530 may be controlled similarly to the heaters of the compartments of the humidification arrangements described above. Preferably, both the movement of both of the first and second panels 552, 554 and the activation of the one or more heaters 530 may be controlled according to the same desired set points and/or according to other input signals received by a controller controlling the operation of the humidification arrangement 512.

The one or more moisture sources are not necessarily limited to being located at the bottom of the humidification arrangement housing as pictured in FIG. 5 but could also be located on the sides or top of the arrangement housing. Similarly, moving panels could be located on the sides or top of the arrangement housing. Moisture could be retained using a semi-permeable membrane permitting only moisture in the vapor phase to escape from the moisture source.

Figure 10:
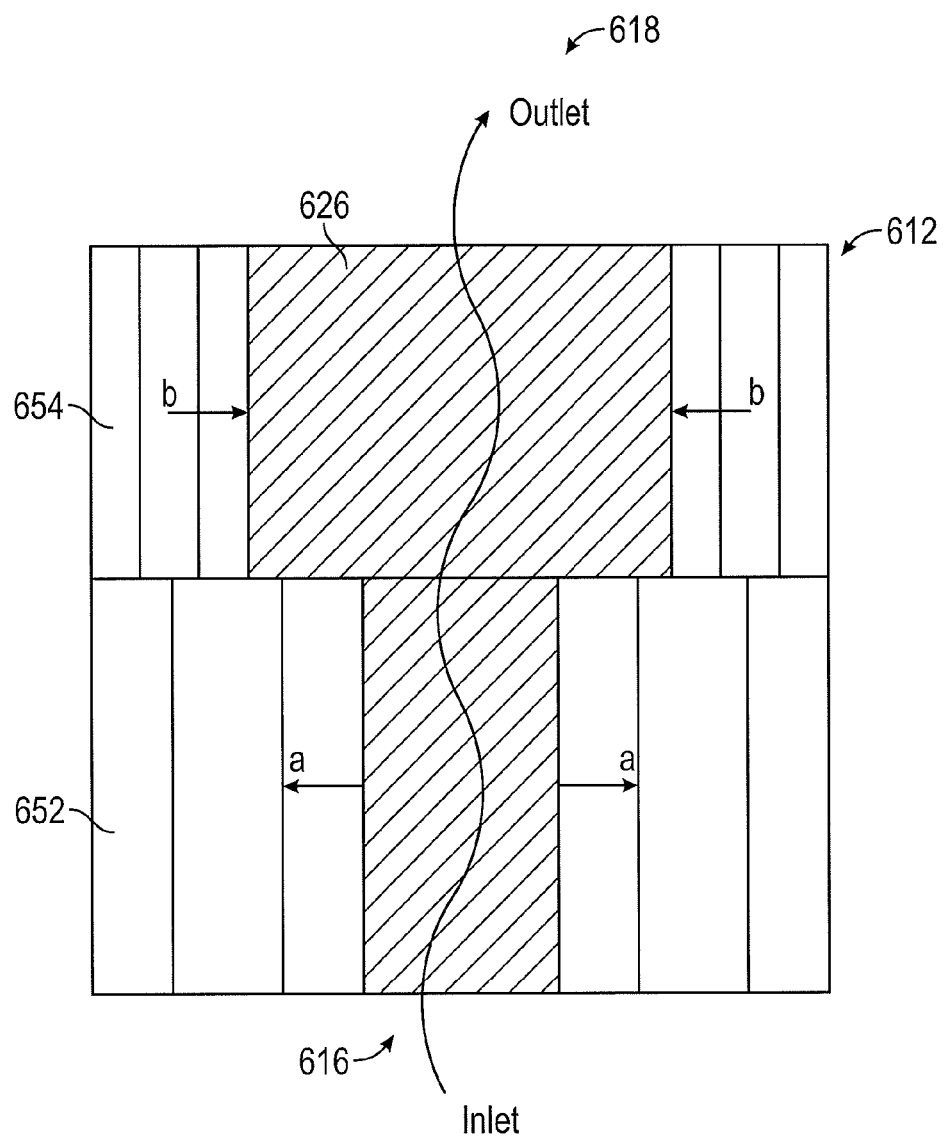
FIG. 10 is a schematic top view of a humidification system.
Figure 11:
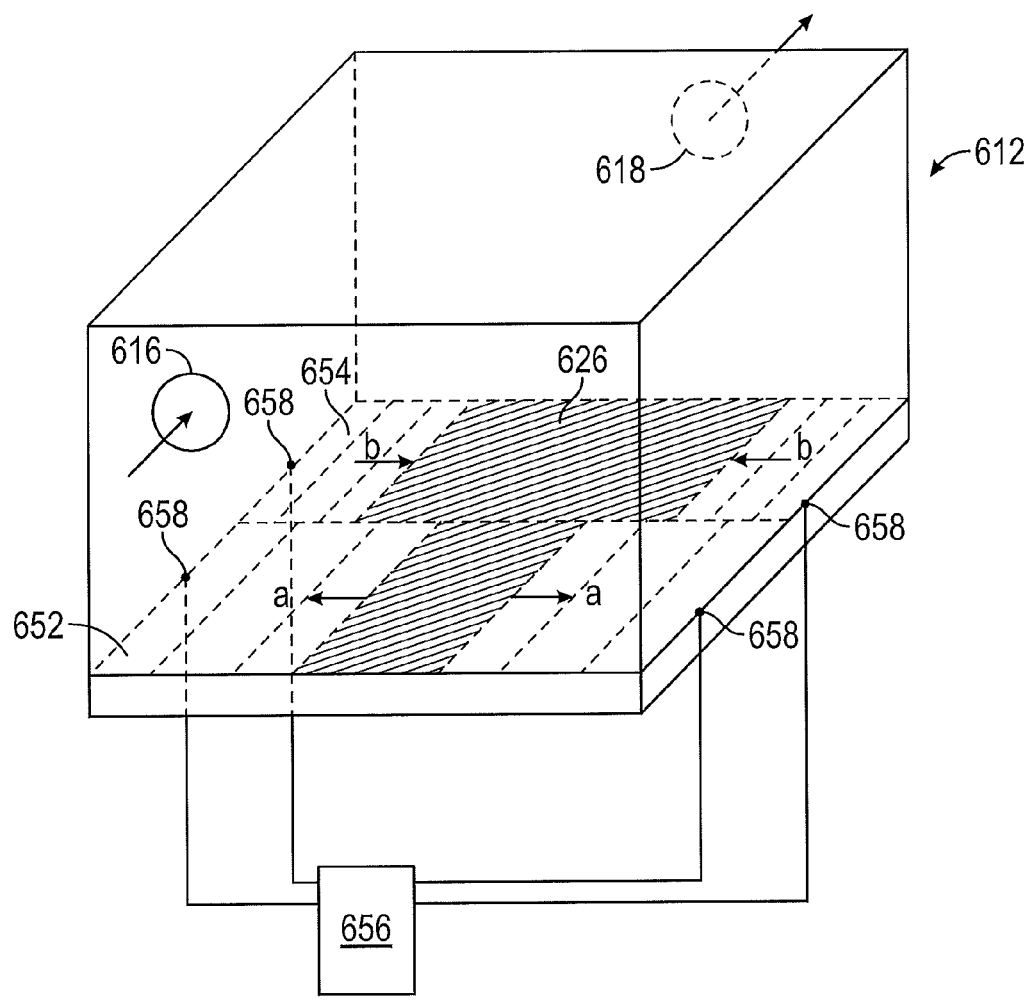
FIG. 11 is schematic perspective view of the humidification system of FIG. 10.

With reference now to FIGS. 10 and 11, another configuration for a humidification arrangement 612 is illustrated. As will be explained, and similar to the configuration of FIG. 5, the humidification arrangement 612 also modulates the exposed surface area of the water. As such, the moisture output of the humidification arrangement 612 may be adjusted by changing the surface area of the moisture source that is exposed to the gas flow passing through one or more compartments of the humidification arrangement. However, instead of using each individual panel to allow access to a humidification stage (or modulate the humidity output of a stage), the sets of panels 652, 654 could be used to control the exposed surface area of the water, where each set 652, 654 is located part-way between the inlet 616 and the outlet 618 of the humidification arrangement 612. This embodiment requires only a single water reservoir or chamber 626.

As seen in FIG. 11, the single reservoir 626 lies at the bottom of the humidification arrangement 612. Electromechanical panels 652, 654 can have any suitable configuration. In some configurations, one or more of the sets of panels 652, 654 could be a stacked panel configuration with pistons or other actuators 658 that can be extended or contracted by driving an AC motor. The panels 652, 654 can be used to selectively expose portions of the top surface of the reservoir 626 of water. Each of the sets of electromechanical panels 652, 654 could move towards each other or apart from each other (independent movement also possible as disclosed in FIG. 5). The movement of the sets of panels 652, 654 could be set to a function of a humidity set point by linking the actuator of each panel to a controller 656. The controller can be configured in a similar manner to any of the controllers described herein. In some configurations the chamber 626 may be heated and/or multiple chambers and/or multiple reservoirs might be used to improve the output humidity resolution.

It should be understood that the panels 652, 654 may be configured to selectively expose parts of the surface of the water in the chamber 626 in other ways. For example, the panels may in a default stage entirely occlude the surface and may be constructed from an electroactive polymer that contracts upon the application of electrical energy, where the amount of energy applied would be a function of the humidity set point (this would require fewer moving parts). Or vice versa, the polymer could expand upon the application of electrical energy (which allows for at least some humidity via cold pass-over upon failure of electrical systems). The material used for the panels might be electromechanically anisotropic such that expansion or contraction only occurs in a single direction. In some configurations, the panels can roll out to cover the water surface or roll back (that is, toward the walls) to uncover the water surface. Any other suitable configuration also can be used.

Figure 12:
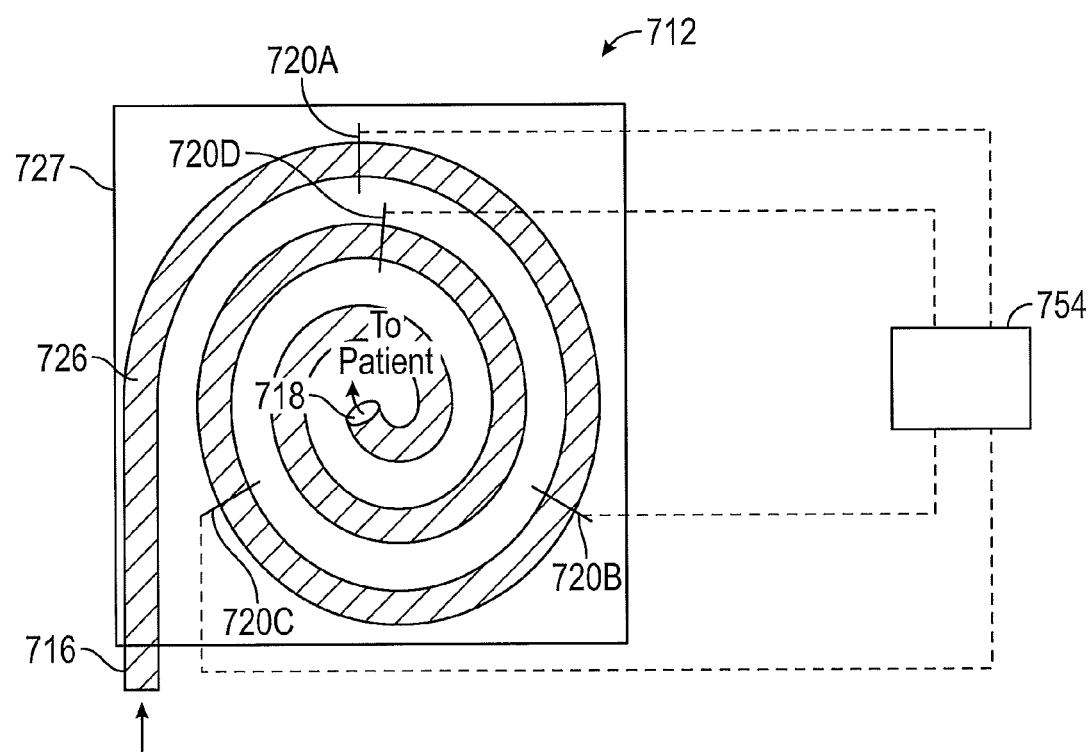
FIG. 12 is a schematic top view of a humidification system.

With reference now to FIG. 12, a further humidification arrangement 712 is illustrated. The illustrated configuration comprises a housing 727. The housing 727 includes a coiled or spiral flow path 726 extending between a gases inlet 716 and a gases outlet 718. The coiled or spiral flow path 726 also can extend upwardly (that is, can be configured to come upwardly out of the page). The illustrated spiral flow path 726 improves usage of humidification space defined within the housing 727. Gas passing through the spiral flow path 726 increases in humidity as it moves over the water in the bottom of the spiral flow path 726.

In some configurations, control of the exposed surface area of water can be provided along the flow path 726. In the illustrated humidification arrangement 712, one or more valves 720A, 720B, 720C, 720D can be positioned along the flow path 726. The valves 720A, 720B, 720C, 720D can be used to define humidification stages (e.g. 1st stage between gases inlet 716 and 1st valve 720A, 2nd stage between 1st and 2nd valves 720A, 720B, and so on) that operate to define chambers. The valves 720A, 720B, 720C, 720D can be configured to direct gases either to the gases outlet 718 or further downstream to pick up more moisture, and similarly the valves 720A, 720B, 720C, 720D might be controlled by a central controller 754 (or via individual controllers, comparing sensed humidity levels at each 'check point' against a set point) to achieve a humidity set point (e.g. a desired humidity value). Other configurations also are possible.

In some configurations, multiple stage humidification arrangements (including the humidification arrangements 212, 312, 412, 512, 612, 712 described above) may be configured such that multiple compartments in series may be used. Each compartment of the humidification arrangement may comprise a controller, a moisture source, a heater adapted to heat the moisture source or a cover adapted to alter the exposed surface area, and, in some configurations, a gas conduit, passage or aperture that may be used to connect each compartment to the next compartment in the series of compartments or to, for example, a patient interface (in the case of the last compartment). One or more of the gas conduits may comprise a conduit heater that may be used to minimize the condensation or moisture along the walls of the conduit. Each compartment may be linked such that the controller of the compartment may communicate with the controllers of one or more other compartments.

For example, a first compartment controller may be linked to a second compartment controller (configured to control, for example, a second compartment downstream of the first compartment) via a wired data communication connection, such as an Ethernet connection (for example, Powerline Ethernet according to the Homeplug AV2-IEEE 1901 standard) or a USB connection, for example, or via a wireless data communication connection, such as WiFi, Bluetooth, or NFC, for example. In some configurations, the multiple stage humidification arrangement may be configured such that the communication connections are used to allow the compartments to interact according to a 'client/server' relationship or according to a 'master/slave' relationship. In other words, the controller for a given compartment may serve to direct the operation of the controllers of one or more subsequent compartments located downstream of the given compartment, and in turn the operation of the controller for the given compartment may be directed or controlled by the controllers of one or more preceding compartments located upstream of the given compartment. In some configurations, the controller of a given compartment may be used to direct the operation of controllers of one or more preceding compartments upstream of the given compartment, and the operation of the controller of the given compartment may in turn by directed by controllers of one or more subsequent compartments.

Figure 13:
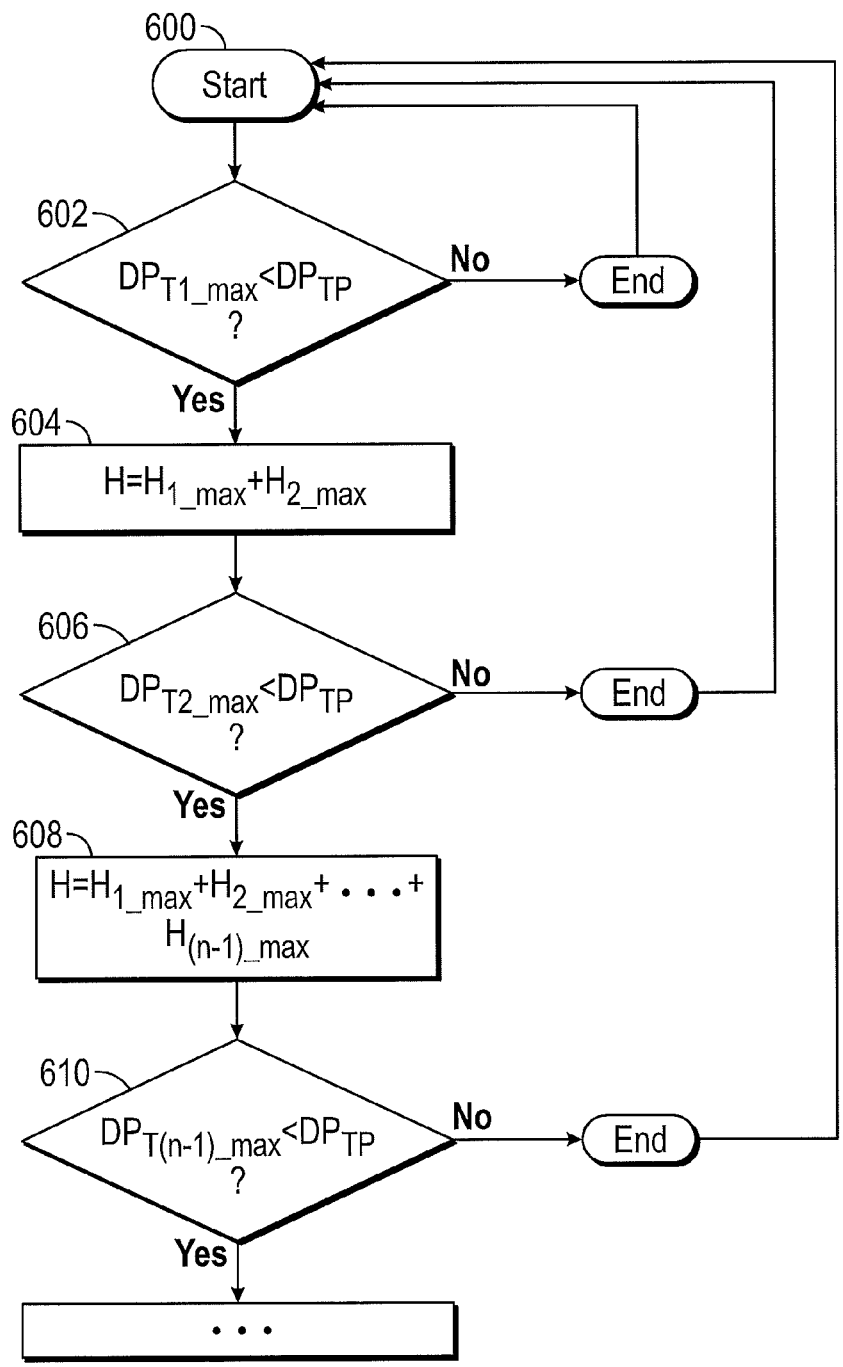
FIG. 13 shows an algorithm for use with a humidification system.

FIG. 13 demonstrates an algorithm that may be used to direct the operation of a multiple stage humidification arrangement as described above. The algorithm may be continuously repeated in order to direct the operation of the humidification arrangement such that the desired output gas characteristics may be achieved under a variety of flow rates and for varying input gas conditions.

In step 600 of the algorithm, the controller controlling the first compartment may prepare to check to see if the moisture and/or heat output of the first compartment may be sufficient for a given gas flow. For example, a desired $DP_{Tp}$ (for example, dew point or moisture output value) that should be received by a patient utilizing the humidification arrangement as part of a respiratory therapy system may be calculated. A $DP_{T1\_max}$ value (for example, dew point or humidity output value) representing the maximum moisture output of the first compartment for a given flow rate may also be calculated. The $DP_{T1\_max}$ may be a function of the flow rate of gases entering the first compartment, of the temperature of gases entering the first compartment, of the temperature of gases outside of the gas passageway of the first compartment (for example, of gases in the ambient environment), of the velocity of gas passageway of the first compartment (for example, of gases in the ambient environment), of the maximum heat output of the heater of the first compartment, and/or of one or more other variables. These variables may be acquired by using various sensors or sensing modules as described above, for example.

In step 602, the maximum moisture output of the first compartment may be checked to see if it will be sufficient to meet the desired moisture output of the humidification arrangement (e.g, if $DP_{T1\_max} < DP_{Tp}$). If the maximum moisture output of the first compartment meets or exceeds the desired moisture output of the humidification arrangement, the instant iteration of the algorithm may end and step 600 may be repeated after a predetermined period of time (for example, 10 milliseconds). If the maximum moisture output of the first compartment is less than the desired moisture output of the humidification arrangement, then the next step 604 of the algorithm may be processed.

In step 604, a combinatorial heat output value H may be calculated. The heat output value H may be the sum of the maximum heat output of the first compartment $H_{1\_max}$ and the maximum heat output of the second compartment $H_{2\_max}$. In some configurations, the heat output values H, $H_{1\_max}$, and $H_{2\_max}$ may comprise the combinatorial power rating of the heaters (for example, resistive heating elements or otherwise) of the humidification arrangement and the maximum power ratings of the heaters of the compartments, respectively. A $DP_{T2\_max}$ value representing the maximum moisture output of the combination of the first and second compartments may be calculated as a function of the heat output value H.

In step 606, similarly to the check performed in step 602, the $DP_{T2\_max}$ may be compared to the $DP_{TP}$ to check that the combined moisture output of the first and second compartments can meet the desired moisture output value. If the desired moisture output value is achievable, the first and second compartments may be configured to meet the desired moisture output and the algorithm may loop as in step 602. Similarly, if the desired moisture output value is not achievable with the first and second compartments, steps 608 and 610 may be performed to check if a third compartment is sufficient to achieve a desired moisture output.

It should be understood that any number of compartments or stages may be used with the given algorithm. A controller directing the algorithm may determine that the number of compartments present is insufficient and direct a user of the humidification arrangement to attach one or more additional compartments to the humidification arrangement (for example, via a user interface or output module of the humidification arrangement or another component linked to the humidification arrangement). Conversely, a controller directing the algorithm may determine that the number of compartments present is greater than necessary to provide an adequate level of moisture to gases passing through the humidification arrangement and cut off power to one or more of the compartments (for example, first compartments) in the series.

Alternatively, the humidification arrangement may comprise a valving arrangement that may be used to divert the flow entering the humidification arrangement such that it bypasses one or more of the compartments (for example, first compartments) in the series. In some cases, multiple controllers controlling individual partitions may be used, and each controller may process certain steps of the algorithm. For example, the controller for the first compartment may perform steps 600 and 602, and if the moisture output is determined to be insufficient, the heat output of the heater of the first compartment may be set to a maximum value and the controller for the second compartment may receive the $H_{1\_max}$ value of the first compartment and perform steps 604 and 606. If the output of the two compartments is still determined to be insufficient, the heat output of the heater of the second compartment may be set to a maximum value and the controller for the third compartment may perform steps 608 and 610. As implied, any number of compartments may be used in this manner.

Figure 4:
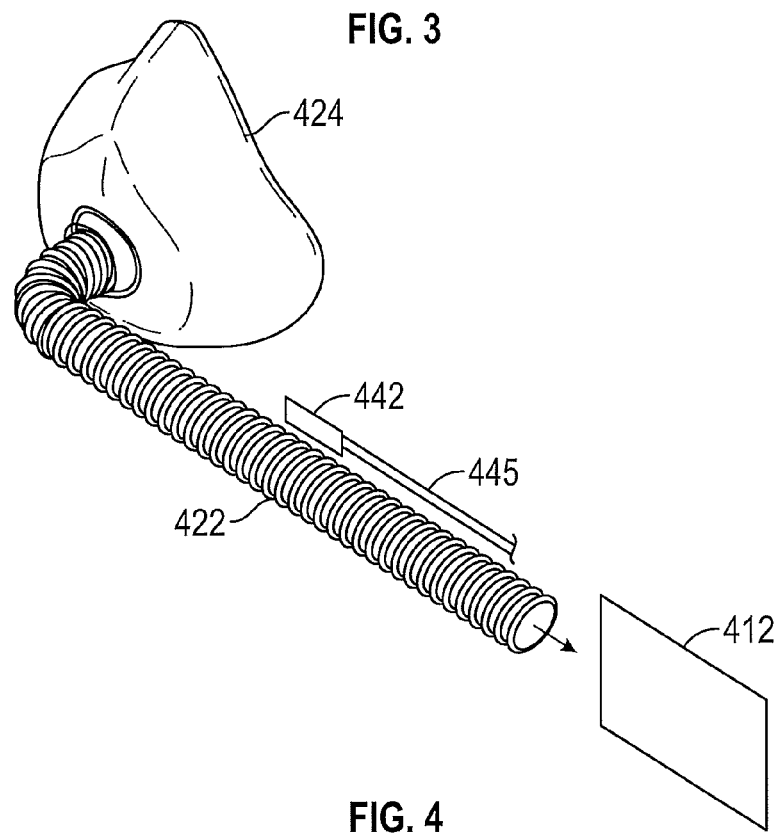
FIG. 4 shows a portion of a respiratory therapy system.

Some condensation of moisture may occur, for example, in a conduit connecting the humidification arrangement of any of the exemplary configurations above to a respiratory interface, particularly if the environment surrounding the conduit is cold or gases (for example ambient air, etc) are passing along the outer surface of the conduit. FIG. 4 demonstrates a section of a respiratory therapy system comprising a conduit 422 extending between a humidification arrangement 412 and a patient interface 424. The conduit 422 may comprise a conduit heater having an adjustable heat output or duty cycle. The conduit heater may be, for example, a resistive heating wire located in, on, around or near the walls of the conduit 422.

The conduit 422 may comprise a sensing module 442 that may relay information to a controller adapted to control the conduit heater. The information may be relayed through a data connection 445 to the controller. The data connection 445 may comprise a separate data communication wire, may be the resistive heating wire (for example, the current passing through the resistive heating wire may be modulated to encompass the data signal from the sensing module 442), or may comprise a wireless connection. The sensing module 442 may comprise, for example, a flow sensor (which may be an omnidirectional flow sensor) adapted to determine the velocity of gases passing along the flow sensor, a temperature sensor adapted to determine the temperature of gases passing along the temperature sensor, or a condensation sensor adapted to determine the presence or degree of condensate in the conduit 422. The signals obtained from the sensing module 442 may be used to adjust the heat output of the conduit heater, the moisture output of the humidification arrangement 412, the moisture and/or heat output of the compartments of the humidification arrangement 412, and/or other parts of components of the respiratory therapy system.

Certain features, aspects, and advantages of the above configurations described with reference to the accompanying figures describe multiple stage humidification systems. In other configurations, multiple stage gas conditioning systems are envisioned. Multiple stage gas conditioning systems may comprise multiple stages, where each stage is adapted to modulate a quantity or value of a gas characteristic or substance in a gas flow to deliver a desired or target gas characteristic or substance. The gas characteristic may include a number of characteristics, including but not limited to temperature, humidity, dew point, enthalpy, pressure, velocity, density, and viscosity. The substance may include a number of substances, including but not limited to medications, excipients, surfactants, adjuvants, aerosols, and gases per se. Each stage of the multiple stage gas conditioning system may be configured to add or subtract a quantity or value of the gas characteristic or substance to achieve the target gas characteristic or substance.

As an example, a multiple stage gas conditioning system may be configured to modulate the temperature of a gas flow passing through the multiple stage gas conditioning system to reach a target output gas temperature. The multiple stage gas conditioning system might comprise first and second stages, each stage comprising a gas heater. In this configuration, each stage might not be configured to humidity the gas flow. The heaters of each stage might be controlled by a controller such that they are controlled according to a single control strategy to meet the target output gas temperature. By using multiple stages to modulate the temperature of the gas flow, where each stage is controlled according to a single control strategy, fine control of the temperature of the gas flow can be achieved. Additionally, the use of such a control strategy can permit the temperature of the gas flow to rapidly change in response to changing target output gas temperatures. For example, if it is desired that a high gas temperature be delivered in synchronicity with an inhalation of a patient and a low gas temperature be delivered in synchronicity with an exhalation of the patient, the thermal inertia of a heater in a single stage gas conditioning system may be too high to rapidly bring about appropriate changes in output gas temperature. However, if a multiple stage gas conditioning system with such a control strategy is utilized, the desired changes in output gas temperature might be achieved while maintaining fine control of the output gas temperature. Each stage of the multiple stage gas conditioning system might be configured to contribute a determined amount of heat to the gas flow (the heat contribution of any one stage being dependent on the control strategy, which for example might be a function of an input gas temperature determined via use of a temperature sensor).

As another example, a multiple stage gas conditioning system might be configured to modulate a quantity of a medicament in a gas flow passing through the multiple stage gas conditioning system to reach a target output medicament dosage. In some cases, it might be desired to add nebulized medicament to the gas flow. If nebulized medication is added distal to a patient receiving the gas flow, although fine control of the temperature and humidity of the gas flow containing the medication might be achieved, in some cases 'rain-out' or deposition of the medication along walls of a gas passageway or conduit might be problematic. If nebulized medication is added proximal to the patient receiving the gas flow, rain-out of the medication may be less problematic, but the temperature and humidity of the gas flow can become more difficult to control. By using multiple stages to add, for example, nebulized medicament to the gas flow (one stage being more proximal to the patient, and another stage being more distal from the patient), where each stage is controlled according to a single control strategy, the target medicament dosage might be more reliably achieved while maintaining desired gas characteristics.

In still other configurations, the multiple stage gas conditioning system might be configured to modulate quantities or values of gas characteristics or substances in a gas flow passing through the multiple stage gas conditioning system, where each stage is configured to modulate the quantity or value of a different gas characteristic or substance. For example, a multiple stage gas conditioning system might comprise a first stage adapted to add nebulized medication and humidity to the gas flow and a second stage adapted to add humidity to the gas flow. Both a target output humidity and target output medication dosage might be sought. The second stage might be downstream of the first stage. The second stage might be more proximal to the patient.

It may be desired to finely control the particle size of the nebulized medication entrained in the gas flow to optimize its delivery to the patient. Generally, smaller particles are more effective than larger particles at reaching small portions of a patient's airway (e.g. the alveoli). However, small particles can be more likely to 'rain-out' or be deposited along walls of a gas passageway or conduit of the multiple stage gas conditioning system. In some cases, the particle size may be controlled by managing the enthalpy of the gas flow. Increasing the enthalpy of the gas flow can decrease the particle size of a nebulized medicament entrained in the gas flow. If nebulized medication is added to the gas flow at the first stage, humidity might additionally be added to the first stage such that some progress towards meeting the target output humidity might be made while minimizing the particle size reduction of the medication (thereby reducing potential 'rain-out' problems). Adjusting the humidity contribution of the second stage can further promote achievement of the target output humidity while effectively postponing the reduction in medication particle size (due to increasing gas enthalpy). If a single control strategy can be used to modulate the humidity and medicament contributions of the first and second stages of the multiple stage gas conditioning system to the gas flow passing through the multiple stage gas conditioning system, improved medicament delivery can be achieved while achieving acceptable output humidity.

Unless the context clearly requires otherwise, throughout the description and the claims, the words "comprise", "comprising", and the like, are to be construed in an inclusive sense as opposed to an exclusive or exhaustive sense, that is to say, in the sense of "including, but not limited to."

Where, in the foregoing description reference has been made to integers or components having known equivalents thereof, those integers or components are herein incorporated as if individually set forth.

The disclosed methods, apparatus and systems may also be said broadly to comprise the parts, elements and features referred to or indicated in the disclosure, individually or collectively, in any or all combinations of two or more of said parts, elements or features.

Reference to any prior art in this specification is not, and should not be taken as, an acknowledgement or any form of suggestion that that prior art forms part of the common general knowledge in the field of endeavour in any country in the world.

Although the present disclosure has been described in terms of certain embodiments, other embodiments apparent to those of ordinary skill in the art also are within the scope of this disclosure. Thus, various changes and modifications may be made without departing from the spirit and scope of the disclosure. For instance, various components may be repositioned as desired. Moreover, not all of the features, aspects and advantages are necessarily required to practice the present disclosure. Accordingly, the scope of the present disclosure is intended to be defined only by the claims that follow.

What is claimed is:

1. A respiratory humidification arrangement comprising:
a gas passageway extending between a first location and a second location, the gas passageway comprising an inspiratory pathway configured to interface with an airway of a patient, the inspiratory pathway comprising a first compartment and a second compartment, each compartment comprising a moisture source configured to add moisture to gases in the gas passageway, each moisture source having an adjustable moisture output, wherein the adjustable moisture outputs are configured to be independently controlled;
a sensor adapted to sense one or more characteristic or substance of a gases flow; and
a controller adapted to control the adjustable moisture output of at least one of the first compartment and the second compartment based on data from the sensor to deliver a target gas characteristic or substance, wherein the moisture source of the first compartment and/or the second compartment comprises a liquid reservoir configured to hold a volume of a liquid, wherein the controller is adapted to control an actuator that varies an exposed surface area of the liquid to gases passing over the volume of the liquid, wherein the liquid reservoir is configured to add moisture to gases passing over the volume of the liquid.

2. The respiratory humidification arrangement of claim 1, wherein the moisture source of the first compartment and the moisture source of the second compartment are separate from each other.

3. The respiratory humidification arrangement of claim 1, wherein the moisture source of the first compartment and the moisture source of the second compartment are in fluid communication with each other.

4. The respiratory humidification arrangement of claim 1, comprising a heater configured to heat at least one of the first compartment and the second compartment.

5. The respiratory humidification arrangement of claim 4, wherein the heater is configured to heat the first compartment and the second compartment.

6. The respiratory humidification arrangement of claim 1, wherein the first compartment and the second compartment are integrated into a single housing.

7. The respiratory humidification arrangement of claim 6, wherein the first compartment and the second compartment are isolated from each other by a partition.

8. The respiratory humidification arrangement of claim 1, wherein the first compartment is defined within a first housing and the second compartment is defined within a second housing, and the first housing is separate and distinct from the second housing.

9. The respiratory humidification arrangement of claim 1, wherein the gas passageway comprises a tube that connects the first compartment to the second compartment, and wherein the tube connects an outlet of the first compartment to an inlet of the second compartment.

10. The respiratory humidification arrangement of claim 1, wherein the gas passageway comprises one or more valves that direct flow through the humidification arrangement.

11. The respiratory humidification arrangement of claim 1, wherein the sensor is positioned adjacent to a port of the humidification arrangement and wherein the port is an outlet of the humidification arrangement.

12. The respiratory humidification arrangement of claim 1, wherein the sensor is positioned adjacent to the first compartment or the second compartment.

13. The respiratory humidification arrangement of claim 1, wherein the sensor is positioned to be in fluid communication with the gas passageway adjacent a passage into or out of the first compartment or the second compartment.

14. The respiratory humidification arrangement of claim 1, wherein the sensor is positioned to be in fluid communication with the gas passageway at a location between a first compartment passageway and a second compartment passageway.

15. The respiratory humidification arrangement of claim 14, wherein the first compartment and the second compartment are connected in series, and wherein the sensor is adapted to measure at least one of gases temperature, humidity, or flow rate.

16. The respiratory humidification arrangement of claim 1, wherein the target gas characteristic or substance is a temperature level or a humidity level.

17. The respiratory humidification arrangement of claim 1, wherein the controller is mounted to or connected to a housing that envelopes the first compartment and the second compartment.

18. The respiratory humidification arrangement of claim 1, wherein the controller is associated with one of the first compartment and the second compartment, and wherein the controller is adapted to control the humidification arrangement.

19. The respiratory humidification arrangement of claim 1, comprising a heater, wherein the controller is adapted to vary an output of the heater.

20. The respiratory humidification arrangement of claim 1, wherein the actuator is adapted to move a partition or panel.

21. The respiratory humidification arrangement of claim 1, wherein the controller is adapted to vary a flow path through the humidification arrangement by controlling one or more valves within the humidification arrangement.

22. The respiratory humidification arrangement of claim 1, wherein the controller is adapted to:
receive data from the sensor;
determine a control strategy as a function of the data received from the sensor and the target gas characteristic or substance being delivered; and
control a level of the target gas characteristic or substance generated by each of the first and second compartments based upon the determined control strategy.

23. The respiratory humidification arrangement of claim 22, wherein the controller is further adapted to control an amount of moisture by varying a heater output of the first compartment or the second compartment.

24. The respiratory humidification arrangement of claim 22, wherein the controller is further adapted to control whether a compartment of the first and second compartments contributes moisture by altering the gas passageway.

25. The respiratory humidification arrangement of claim 24, wherein the controller is further adapted to control whether the compartment of the first and second compartments contributes moisture by bypassing or passing gases through the compartment.

26. The respiratory humidification arrangement of claim 22, wherein the controller is further adapted to determine a common control strategy for the first compartment and the second compartment of the system.

27. The respiratory humidification arrangement of claim 22, wherein the controller is further adapted to determine independent control strategies for each of the first compartment and the second compartment.

28. The respiratory humidification arrangement of claim 22, wherein the controller is further adapted to determine a control strategy based upon the target gas characteristic or substance specific to a compartment of the first and second compartments.

29. The respiratory humidification arrangement of claim 22, wherein the controller is further adapted to use a stage target that represents a desired amount to increase the target gas characteristic or substance for the gases flowing through the first compartment or the second compartment.

30. The respiratory humidification arrangement of claim 22, wherein the controller is further adapted to use the target gas characteristic or substance that is a target temperature level or a target humidity level.

31. The respiratory humidification arrangement of claim 22, wherein the controller is further adapted to use sensor data that represents at least one of a temperature level, a humidity level, and a flow rate.

32. The respiratory humidification arrangement of claim 22, wherein the controller is further adapted to use sensor data that is measured at an inlet to the gas passageway.

33. The respiratory humidification arrangement of claim 22, wherein the controller is further adapted to use sensor data that is measured at an outlet of the gas passageway.

* * * * *

UNITED STATES PATENT AND TRADEMARK OFFICE
CERTIFICATE OF CORRECTION

PATENT NO. : 11,173,272 B2
APPLICATION NO. : 15/303719
DATED : November 16, 2021
INVENTOR(S) : Anthony James Newland et al.

Page 1 of 1

It is certified that error appears in the above-identified patent and that said Letters Patent is hereby corrected as shown below:

On the Title Page

On Page 2, Column 2 (Item (56) U.S. Patent Documents), Line 18, delete "Pel" and insert --Kopel--.

On Page 3, Column 1 (Item (56) U.S. Patent Documents), Line 57, delete "Henryetai." and insert --Henry et al.--.

In the Claims

In Column 26, Line 9, In Claim 26, after "compartment" delete "of the system.".

Signed and Sealed this
Eighth Day of February, 2022

Drew Hirshfeld
*Performing the Functions and Duties of the
Under Secretary of Commerce for Intellectual Property and
Director of the United States Patent and Trademark Office*